US011452767B2

(12) United States Patent
Olweus et al.

(10) Patent No.: US 11,452,767 B2
(45) Date of Patent: Sep. 27, 2022

(54) CTL PEPTIDE EPITOPES AND ANTIGEN-SPECIFIC T CELLS, METHODS FOR THEIR DISCOVERY, AND USES THEREOF

(71) Applicant: Oslo universitetssykehus HF, Oslo (NO)

(72) Inventors: Johanna Olweus, Eiksmarka (NO); Shraddha Kumari, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 632 days.

(21) Appl. No.: 15/037,007

(22) PCT Filed: Nov. 14, 2014

(86) PCT No.: PCT/IB2014/003021
§ 371 (c)(1),
(2) Date: May 16, 2016

(87) PCT Pub. No.: WO2015/071763
PCT Pub. Date: May 21, 2015

(65) Prior Publication Data
US 2016/0263205 A1 Sep. 15, 2016

Related U.S. Application Data

(60) Provisional application No. 61/904,688, filed on Nov. 15, 2013.

(51) Int. Cl.
| | |
|---|---|
| G01N 33/50 | (2006.01) |
| C07K 14/74 | (2006.01) |
| A61K 39/00 | (2006.01) |
| G01N 33/569 | (2006.01) |
| A61K 39/39 | (2006.01) |
| C07K 14/705 | (2006.01) |

(52) U.S. Cl.
CPC .......... *A61K 39/0011* (2013.01); *A61K 39/39* (2013.01); *C07K 14/70503* (2013.01); *C07K 14/70539* (2013.01); *G01N 33/505* (2013.01); *G01N 33/56977* (2013.01); *A61K 2039/5158* (2013.01); *A61K 2039/55527* (2013.01); *A61K 2039/572* (2013.01); *G01N 2333/70539* (2013.01)

(58) Field of Classification Search
None
See application file for complete search history.

(56) References Cited

FOREIGN PATENT DOCUMENTS

| WO | 00/17639 | 3/2000 |
| WO | 2004/084838 | 10/2004 |

OTHER PUBLICATIONS

Abrahamsen et al (Int. J. Cancer, 130: 1821-1832, Apr. 15, 2012, published online May 31, 2011) (Year: 2012).*
Bae et al (Clin. Cane. Res. 2005, 11: 1629-1638) (Year: 2005).*
Ruedi, A. (Nature, 2003,422: 115-116) (Year: 2003).*
Kalos and June (Immunity, 2013, 39: 49-60) (Year: 2013).*
Morel et al (Immunity 12: 107-117, 1/00) (Year: 2000).*
Kraemer et al. (Stem Cells Int., 2015, art. ID 346714, pp. 1-12) (Year: 2015).*
Liao et al (Molec. Ther., 2004, 9(5): 757-764) (Year: 2004).*
Hadrup et al (Nat. Methods, 2009, 6(7): 520-526) (Year: 2009).*
Stripecke, R (Meth. Molec. Biol, Method and Protocol, C. Baum (ed.), 506, chapter 11, pp. 139-158, Humana Press, 2009) (Year : 2009).*
Heemskerk, M. (Haematologica, 2010, 95(1): 15-19) (Year: 2010).*
UniProtKB—P11836 (2021) (Year: 2021).*
UniProtKB—P05164 (2021) (Year: 2021).*
Yacoub et al. (J. Gene Med. 2007, 9: 579-584) (Year: 2007).*
Meng et al. (Nature.com, Scientific Reports, 2016, 6:19750, pp. 1-12) (Year: 2016).*
Wu et al. (Mol. Ther. 2010, 18(1): 80-86) (Year: 2010).*
Chauxetal (J. Immunol. 1999, 163: 2928-2936) (Year: 1999).*
Lundegaarde et al. (Immunol. 2010, 130: 309-318) (Year: 2010).*
Bakker et al. (PNAS, 2008, 105(10): 3825-3830) (Year: 2008).*
DiBrino et al (Biochem. 1995, 34: 10130-10138) (Year: 1995).*
Romero et al. (J. Exp. Med. 1998, 188: 1641-1650) (Year: 1998).*
Admon, A & Bassani-Sternberg, M (2011) The Human Immunopeptidome Project, a suggestion for yet another postgenome next big thing. Mol Cell Proteomics 10(10):O111 011833.
International Search Report and Written Opinion, International Patent Application No. PCT/IB2014/003021, dated Aug. 21, 2015.
Kessler JH & Melief CJ (2007) Identification of T-cell epitopes for cancer immunotherapy. Leukemia 21 (9):1859-1874.
Kumari, S. et al. "Alloreactive cytotoxic T cells provide means to decipher the immunopeptidome and reveal a plethora of tumor-associated self-epitopes" Proceedings of the National Academy of Sciences, vol. 111, No. 1, Dec. 16, 2013, pp. 403-408.
Lundegaard C, et al. (2008) NetMHC-3.0: accurate web accessible predictions of human, mouse and monkey MHC class I affinities for peptides of length 8-11. Nucleic acids research 36(Web Server issue):W509-512.
Lundegaard, C. et al. "Prediction of epitopes using neural network based methods", Journal of Immunological Methods, vol. 374, No. 1-2, Sp. Iss. SI, Nov. 2011, pp. 26-34.

(Continued)

*Primary Examiner* — G. R. Ewoldt
*Assistant Examiner* — Marianne DiBrino
(74) *Attorney, Agent, or Firm* — Casimir Jones S.C.; J. Mitchell Jones

(57) ABSTRACT

The present invention relates to CTL peptide epitopes, high-throughput methods for their identification, and their uses. In particular, the present invention relates to peptide epitopes for cancer immunotherapy and Hepatitis C Virus vaccines. The present invention also relates to methods and systems for identifying antigen-specific CTLs.

11 Claims, 9 Drawing Sheets
Specification includes a Sequence Listing.

(56) References Cited

OTHER PUBLICATIONS

Maher et al., "Targeting cytotoxic T lymphocytes for cancer immunotherapy" Br J Cancer Aug. 31, 2004; 91(5): 817-821.

Nielsen M, et al. (2007) NetMHCpan, a method for quantitative predictions of peptide binding to any HLA-A and -B locus protein of known sequence. PloS one 2(8):e796.

Overwijk et al., "Tumor Regression and Autoimmunity after Reversal of a Functionally Tolerant State of Self-reactive CD8+ T Cells" J Exp Med. Aug. 18, 2003; 198(4): 569-580.

Rivino, L. et al. "Defining CD8+ T Cell Determinants during Human Viral Infection in Populations of Asian Ethnicity" The Jounral of Immunology, vol. 191, No. 8, Sep. 20, 2013, pp. 4010-4019.

Rosenberg et al., "Cancer immunotherapy: moving beyond current vaccines." Nat Med. Sep. 2004; 10(9): 909-915.

Sadovnikova E, Jopling LA, Soo KS, & Stauss HJ (1998) Generation of human tumor-reactive cytotoxic T cells against peptides presented by non-self HLA class I molecules. Eur J Immunol 28(1): 193-200.

Stronen E, et al. (2009) Dendritic cells engineered to express defined allo-HLA peptide complexes induce antigen-specific cytotoxic T cells efficiently killing tumor cells Scand J Immunol 69(4):319-328.

Toebes M, et al. (2006) Design and use of conditional MHC class I ligands. Nat Med 12(2):246-251.

Wang et al. "CTL epitopes for influenza A including the H5N1 bird flu; genome-pathogen-, and HLA-wide screening", Vaccine, Elsevier LTD, vol. 25, No. 15, Mar. 16, 2007, pp. 2823-2831.

Wilde S, et al. (2009) Dendritic cells pulsed with RNA encoding allogeneic MHC and antigen induce T cells with superior antitumor activity and higher TCR functional avidity. Blood 114(10):2131-2139.

Kumari, S. et al. Alloreactive cytotoxic T cells provide means to decipher the immunopeptidome and reveal a plethora of tumor-associated self-epitopes, PNAS, Jan. 2014, vol. 111, No. 1, 403-408.

Stronen, E. et al. Targeting of cancer neoantigens with donor-derived T cell receptor repertoires, Science, Jun. 2016, vol. 352, issue 6291, 1337-1341.

\* cited by examiner

SEQUENCE LISTING

```
<160> NUMBER OF SEQ ID NOS: 75

<210> SEQ ID NO 1
<211> LENGTH: 9
<212> TYPE: PRT
<213> ORGANISM: homo sapiens

<400> SEQUENCE: 1

Ser Leu Phe Leu Gly Ile Leu Ser Val
1               5

<210> SEQ ID NO 2
<211> LENGTH: 9
<212> TYPE: PRT
<213> ORGANISM: homo sapiens

<400> SEQUENCE: 2

Lys Met Ile Met Asn Ser Leu Ser Leu
1               5

<210> SEQ ID NO 3
<211> LENGTH: 9
<212> TYPE: PRT
<213> ORGANISM: homo sapiens

<400> SEQUENCE: 3

Leu Ile Phe Ala Phe Phe Gln Glu Leu
1               5
```

```
<210> SEQ ID NO 4
<211> LENGTH: 9
<212> TYPE: PRT
<213> ORGANISM: homo sapiens

<400> SEQUENCE: 4

Gln Ile Met Asn Gly Leu Phe His Ile
1               5

<210> SEQ ID NO 5
<211> LENGTH: 9
<212> TYPE: PRT
<213> ORGANISM: homo sapiens

<400> SEQUENCE: 5

Tyr Ile Ile Ser Gly Ser Leu Leu Ala
1               5

<210> SEQ ID NO 6
<211> LENGTH: 9
<212> TYPE: PRT
<213> ORGANISM: homo sapiens

<400> SEQUENCE: 6

Pro Leu Trp Gly Gly Ile Met Tyr Ile
1               5

<210> SEQ ID NO 7
<211> LENGTH: 9
<212> TYPE: PRT
<213> ORGANISM: homo sapiens

<400> SEQUENCE: 7

Ser Leu Phe Ala Ala Ile Ser Gly Met
1               5

<210> SEQ ID NO 8
<211> LENGTH: 9
<212> TYPE: PRT
<213> ORGANISM: homo sapiens

<400> SEQUENCE: 8

Leu Met Ile Pro Ala Gly Ile Tyr Ala
1               5

<210> SEQ ID NO 9
<211> LENGTH: 9
<212> TYPE: PRT
<213> ORGANISM: homo sapiens

<400> SEQUENCE: 9

Ile Met Asn Ser Leu Ser Leu Phe Ala
1               5

<210> SEQ ID NO 10
<211> LENGTH: 9
<212> TYPE: PRT
<213> ORGANISM: homo sapiens

<400> SEQUENCE: 10

Phe Leu Gly Ile Leu Ser Val Met Leu
1               5

<210> SEQ ID NO 11
<211> LENGTH: 9
```

```
<212> TYPE: PRT
<213> ORGANISM: homo sapiens

<400> SEQUENCE: 11

Gly Leu Leu Met Ile Pro Ala Gly Ile
1               5

<210> SEQ ID NO 12
<211> LENGTH: 9
<212> TYPE: PRT
<213> ORGANISM: homo sapiens

<400> SEQUENCE: 12

Phe Ile Arg Ala His Thr Pro Tyr Ile
1               5

<210> SEQ ID NO 13
<211> LENGTH: 9
<212> TYPE: PRT
<213> ORGANISM: homo sapiens

<400> SEQUENCE: 13

Ile Leu Ser Val Met Leu Ile Phe Ala
1               5

<210> SEQ ID NO 14
<211> LENGTH: 9
<212> TYPE: PRT
<213> ORGANISM: homo sapiens

<400> SEQUENCE: 14

Met Ile Leu Ser Ile Met Asp Ile Leu
1               5

<210> SEQ ID NO 15
<211> LENGTH: 9
<212> TYPE: PRT
<213> ORGANISM: homo sapiens

<400> SEQUENCE: 15

Ile Met Tyr Ile Ile Ser Gly Ser Leu
1               5

<210> SEQ ID NO 16
<211> LENGTH: 9
<212> TYPE: PRT
<213> ORGANISM: homo sapiens

<400> SEQUENCE: 16

Ile Met Asp Ile Leu Asn Ile Lys Ile
1               5

<210> SEQ ID NO 17
<211> LENGTH: 9
<212> TYPE: PRT
<213> ORGANISM: homo sapiens

<400> SEQUENCE: 17

Ile Met Asn Gly Leu Phe His Ile Ala
1               5

<210> SEQ ID NO 18
<211> LENGTH: 9
<212> TYPE: PRT
<213> ORGANISM: homo sapiens
```

```
<400> SEQUENCE: 18

Ala Ile Ser Gly Met Ile Leu Ser Ile
1               5

<210> SEQ ID NO 19
<211> LENGTH: 9
<212> TYPE: PRT
<213> ORGANISM: homo sapiens

<400> SEQUENCE: 19

Gly Met Ile Leu Ser Ile Met Asp Ile
1               5

<210> SEQ ID NO 20
<211> LENGTH: 9
<212> TYPE: PRT
<213> ORGANISM: homo sapiens

<400> SEQUENCE: 20

Ser Ile Gln Ser Leu Phe Leu Gly Ile
1               5

<210> SEQ ID NO 21
<211> LENGTH: 9
<212> TYPE: PRT
<213> ORGANISM: homo sapiens

<400> SEQUENCE: 21

Lys Leu Leu Leu Ala Leu Ala Gly Leu
1               5

<210> SEQ ID NO 22
<211> LENGTH: 9
<212> TYPE: PRT
<213> ORGANISM: homo sapiens

<400> SEQUENCE: 22

Ala Leu Ala Gly Leu Leu Ala Ile Leu
1               5

<210> SEQ ID NO 23
<211> LENGTH: 9
<212> TYPE: PRT
<213> ORGANISM: homo sapiens

<400> SEQUENCE: 23

Tyr Leu His Val Ala Leu Asp Leu Leu
1               5

<210> SEQ ID NO 24
<211> LENGTH: 9
<212> TYPE: PRT
<213> ORGANISM: homo sapiens

<400> SEQUENCE: 24

Ser Leu Trp Arg Arg Pro Phe Asn Val
1               5

<210> SEQ ID NO 25
<211> LENGTH: 9
<212> TYPE: PRT
<213> ORGANISM: homo sapiens

<400> SEQUENCE: 25
```

Val Leu Thr Pro Ala Gln Leu Asn Val
1               5

<210> SEQ ID NO 26
<211> LENGTH: 9
<212> TYPE: PRT
<213> ORGANISM: homo sapiens

<400> SEQUENCE: 26

Arg Leu Phe Glu Gln Val Met Arg Ile
1               5

<210> SEQ ID NO 27
<211> LENGTH: 9
<212> TYPE: PRT
<213> ORGANISM: homo sapiens

<400> SEQUENCE: 27

Trp Met Gly Gly Val Ser Glu Pro Leu
1               5

<210> SEQ ID NO 28
<211> LENGTH: 9
<212> TYPE: PRT
<213> ORGANISM: homo sapiens

<400> SEQUENCE: 28

Leu Leu Leu Ala Leu Ala Gly Leu Leu
1               5

<210> SEQ ID NO 29
<211> LENGTH: 9
<212> TYPE: PRT
<213> ORGANISM: homo sapiens

<400> SEQUENCE: 29

Leu Ala Leu Ala Gly Leu Leu Ala Ile
1               5

<210> SEQ ID NO 30
<211> LENGTH: 9
<212> TYPE: PRT
<213> ORGANISM: homo sapiens

<400> SEQUENCE: 30

Val Leu Gly Glu Val Asp Thr Ser Leu
1               5

<210> SEQ ID NO 31
<211> LENGTH: 9
<212> TYPE: PRT
<213> ORGANISM: homo sapiens

<400> SEQUENCE: 31

Ser Met Glu Glu Ala Lys Gln Leu Val
1               5

<210> SEQ ID NO 32
<211> LENGTH: 9
<212> TYPE: PRT
<213> ORGANISM: homo sapiens

<400> SEQUENCE: 32

Leu Leu Ser Tyr Phe Lys Gln Pro Val

<210> SEQ ID NO 33
<211> LENGTH: 9
<212> TYPE: PRT
<213> ORGANISM: homo sapiens

<400> SEQUENCE: 33

Leu Met Phe Met Gln Trp Gly Gln Leu
1               5

<210> SEQ ID NO 34
<211> LENGTH: 9
<212> TYPE: PRT
<213> ORGANISM: homo sapiens

<400> SEQUENCE: 34

Leu Leu Asp His Asp Leu Asp Phe Thr
1               5

<210> SEQ ID NO 35
<211> LENGTH: 9
<212> TYPE: PRT
<213> ORGANISM: homo sapiens

<400> SEQUENCE: 35

Gln Ile Asn Ala Leu Thr Ser Phe Val
1               5

<210> SEQ ID NO 36
<211> LENGTH: 9
<212> TYPE: PRT
<213> ORGANISM: homo sapiens

<400> SEQUENCE: 36

Met Val Tyr Gly Ser Glu Glu Pro Leu
1               5

<210> SEQ ID NO 37
<211> LENGTH: 9
<212> TYPE: PRT
<213> ORGANISM: homo sapiens

<400> SEQUENCE: 37

Asn Met Ser Asn Gln Leu Gly Leu Leu
1               5

<210> SEQ ID NO 38
<211> LENGTH: 9
<212> TYPE: PRT
<213> ORGANISM: homo sapiens

<400> SEQUENCE: 38

Phe Gln Asp Asn Gly Arg Ala Leu Leu
1               5

<210> SEQ ID NO 39
<211> LENGTH: 9
<212> TYPE: PRT
<213> ORGANISM: homo sapiens

<400> SEQUENCE: 39

Asn Leu His Asp Asp Pro Cys Leu Leu
1               5

```
<210> SEQ ID NO 40
<211> LENGTH: 9
<212> TYPE: PRT
<213> ORGANISM: homo sapiens

<400> SEQUENCE: 40

Arg Leu Ala Thr Glu Leu Lys Ser Leu
1               5

<210> SEQ ID NO 41
<211> LENGTH: 9
<212> TYPE: PRT
<213> ORGANISM: homo sapiens

<400> SEQUENCE: 41

Lys Ile Val Gly Ala Met Val Gln Ile
1               5

<210> SEQ ID NO 42
<211> LENGTH: 9
<212> TYPE: PRT
<213> ORGANISM: homo sapiens

<400> SEQUENCE: 42

Tyr Leu Pro Leu Val Leu Gly Pro Thr
1               5

<210> SEQ ID NO 43
<211> LENGTH: 9
<212> TYPE: PRT
<213> ORGANISM: homo sapiens

<400> SEQUENCE: 43

Ser Val Asp Pro Arg Ile Ala Asn Val
1               5

<210> SEQ ID NO 44
<211> LENGTH: 9
<212> TYPE: PRT
<213> ORGANISM: homo sapiens

<400> SEQUENCE: 44

Arg Ile Ala Asn Val Phe Thr Asn Ala
1               5

<210> SEQ ID NO 45
<211> LENGTH: 9
<212> TYPE: PRT
<213> ORGANISM: homo sapiens

<400> SEQUENCE: 45

Leu Ile Gln Pro Phe Met Phe Arg Leu
1               5

<210> SEQ ID NO 46
<211> LENGTH: 9
<212> TYPE: PRT
<213> ORGANISM: homo sapiens

<400> SEQUENCE: 46

Arg Leu Asp Asn Arg Tyr Gln Pro Met
1               5

<210> SEQ ID NO 47
```

```
<211> LENGTH: 9
<212> TYPE: PRT
<213> ORGANISM: homo sapiens

<400> SEQUENCE: 47

Arg Val Phe Phe Ala Ser Trp Arg Val
1               5

<210> SEQ ID NO 48
<211> LENGTH: 9
<212> TYPE: PRT
<213> ORGANISM: homo sapiens

<400> SEQUENCE: 48

Val Leu Glu Gly Gly Ile Asp Pro Ile
1               5

<210> SEQ ID NO 49
<211> LENGTH: 9
<212> TYPE: PRT
<213> ORGANISM: homo sapiens

<400> SEQUENCE: 49

Gly Leu Met Ala Thr Pro Ala Lys Leu
1               5

<210> SEQ ID NO 50
<211> LENGTH: 9
<212> TYPE: PRT
<213> ORGANISM: homo sapiens

<400> SEQUENCE: 50

Phe Val Asn Cys Ser Thr Leu Pro Ala
1               5

<210> SEQ ID NO 51
<211> LENGTH: 9
<212> TYPE: PRT
<213> ORGANISM: Hepatitis C virus

<400> SEQUENCE: 51

Phe Leu Leu Ala Leu Leu Ser Cys Leu
1               5

<210> SEQ ID NO 52
<211> LENGTH: 9
<212> TYPE: PRT
<213> ORGANISM: Hepatitis C virus

<400> SEQUENCE: 52

Ala Gln Pro Gly Tyr Pro Trp Pro Leu
1               5

<210> SEQ ID NO 53
<211> LENGTH: 9
<212> TYPE: PRT
<213> ORGANISM: Hepatitis C virus

<400> SEQUENCE: 53

Leu Leu Ser Cys Leu Thr Val Pro Ala
1               5

<210> SEQ ID NO 54
<211> LENGTH: 9
<212> TYPE: PRT
```

<213> ORGANISM: Hepatitis C virus

<400> SEQUENCE: 54

Asn Leu Pro Gly Cys Ser Phe Ser Ile
1               5

<210> SEQ ID NO 55
<211> LENGTH: 10
<212> TYPE: PRT
<213> ORGANISM: Hepatitis C virus

<400> SEQUENCE: 55

Tyr Leu Leu Pro Arg Arg Gly Pro Arg Leu
1               5                   10

<210> SEQ ID NO 56
<211> LENGTH: 9
<212> TYPE: PRT
<213> ORGANISM: Hepatitis C virus

<400> SEQUENCE: 56

Asp Leu Met Gly Tyr Ile Pro Leu Val
1               5

<210> SEQ ID NO 57
<211> LENGTH: 10
<212> TYPE: PRT
<213> ORGANISM: Hepatitis C virus

<400> SEQUENCE: 57

Leu Leu Ala Leu Leu Ser Cys Leu Thr Val
1               5                   10

<210> SEQ ID NO 58
<211> LENGTH: 9
<212> TYPE: PRT
<213> ORGANISM: Hepatitis C virus

<400> SEQUENCE: 58

Gly Pro Arg Leu Gly Val Arg Ala Thr
1               5

<210> SEQ ID NO 59
<211> LENGTH: 9
<212> TYPE: PRT
<213> ORGANISM: Hepatitis C virus

<400> SEQUENCE: 59

Asp Pro Arg Arg Arg Ser Arg Asn Leu
1               5

<210> SEQ ID NO 60
<211> LENGTH: 9
<212> TYPE: PRT
<213> ORGANISM: Hepatitis C virus

<400> SEQUENCE: 60

Phe Leu Ala Thr Cys Ile Asn Gly Val
1               5

<210> SEQ ID NO 61
<211> LENGTH: 9
<212> TYPE: PRT
<213> ORGANISM: Hepatitis C virus

```
<400> SEQUENCE: 61

Tyr Leu Val Ala Tyr Gln Ala Thr Val
1               5

<210> SEQ ID NO 62
<211> LENGTH: 9
<212> TYPE: PRT
<213> ORGANISM: Hepatitis C virus

<400> SEQUENCE: 62

Tyr Met Asn Thr Pro Gly Leu Pro Val
1               5

<210> SEQ ID NO 63
<211> LENGTH: 9
<212> TYPE: PRT
<213> ORGANISM: Hepatitis C virus

<400> SEQUENCE: 63

Gln Met Trp Lys Cys Leu Ile Arg Leu
1               5

<210> SEQ ID NO 64
<211> LENGTH: 9
<212> TYPE: PRT
<213> ORGANISM: Hepatitis C virus

<400> SEQUENCE: 64

Ser Val Ile Asp Cys Asn Thr Cys Val
1               5

<210> SEQ ID NO 65
<211> LENGTH: 9
<212> TYPE: PRT
<213> ORGANISM: Hepatitis C virus

<400> SEQUENCE: 65

Leu Leu Gly Cys Ile Ile Thr Ser Leu
1               5

<210> SEQ ID NO 66
<211> LENGTH: 9
<212> TYPE: PRT
<213> ORGANISM: Hepatitis C virus

<400> SEQUENCE: 66

Phe Ser Leu Asp Pro Thr Phe Thr Ile
1               5

<210> SEQ ID NO 67
<211> LENGTH: 9
<212> TYPE: PRT
<213> ORGANISM: Hepatitis C virus

<400> SEQUENCE: 67

Cys Ile Asn Gly Val Cys Trp Thr Val
1               5

<210> SEQ ID NO 68
<211> LENGTH: 10
<212> TYPE: PRT
<213> ORGANISM: Hepatitis C virus

<400> SEQUENCE: 68
```

Thr Gly Ser Pro Ile Thr Tyr Ser Thr Tyr
1               5                   10

<210> SEQ ID NO 69
<211> LENGTH: 9
<212> TYPE: PRT
<213> ORGANISM: Hepatitis C virus

<400> SEQUENCE: 69

His Ser Lys Lys Cys Asp Glu Leu
1               5

<210> SEQ ID NO 70
<211> LENGTH: 9
<212> TYPE: PRT
<213> ORGANISM: Hepatitis C virus

<400> SEQUENCE: 70

Leu Ile Arg Leu Lys Pro Thr Leu His
1               5

<210> SEQ ID NO 71
<211> LENGTH: 22
<212> TYPE: DNA
<213> ORGANISM: artificial sequence
<220> FEATURE:
<223> OTHER INFORMATION: synthetic

<400> SEQUENCE: 71
caccatgggg gttcccttct tc                                              22

<210> SEQ ID NO 72
<211> LENGTH: 50
<212> TYPE: DNA
<213> ORGANISM: artificial sequence
<220> FEATURE:
<223> OTHER INFORMATION: synthetic

<400> SEQUENCE: 72
tcaggcgtag tcgggcacgt cgtaggggta ggaggcttcc ctccaggaag               50

<210> SEQ ID NO 73
<211> LENGTH: 10
<212> TYPE: PRT
<213> ORGANISM: artificial sequence
<220> FEATURE:
<223> OTHER INFORMATION: synthetic

<400> SEQUENCE: 73

Glu Leu Ala Gly Ile Gly Ile Leu Thr Val
1               5                   10

<210> SEQ ID NO 74
<211> LENGTH: 9
<212> TYPE: PRT
<213> ORGANISM: artificial sequence
<220> FEATURE:
<223> OTHER INFORMATION: synthetic

<400> SEQUENCE: 74

Asn Leu Val Pro Met Val Ala Thr Val
1               5

<210> SEQ ID NO 75
<211> LENGTH: 9
<212> TYPE: PRT

```
<213> ORGANISM: artificial sequence
<220> FEATURE:
<223> OTHER INFORMATION: synthetic

<400> SEQUENCE: 75

Asn Leu Val Pro Met Val Ala Thr Val
1               5
```

CTL PEPTIDE EPITOPES AND ANTIGEN-SPECIFIC T CELLS, METHODS FOR THEIR DISCOVERY, AND USES THEREOF

FIELD OF THE INVENTION

The present invention relates to Cytotoxic T cell (also known as cytotoxic T lymphocytes, CTL) peptide epitopes, high-throughput methods for their identification, and their uses. In particular, the present invention relates to peptide epitopes for cancer immunotherapy and Hepatitis C Virus (HCV) vaccines. The present invention also relates to methods and systems for identifying antigen-specific CTLs.

BACKGROUND OF THE INVENTION

Cytotoxic T cells (CTLs), selectively kill target cells that express defined peptides in complex with major histocompatibility complex (MHC) class I molecules on the cell surface. Most tumor-associated antigens (TAA) are wild type self-proteins, and T cells that recognize peptides from these antigens with high affinity are deleted during thymic development. Thus, the utility of T cells for detection of self-peptides presented on self-HLA is limited by tolerance. The number of epitopes identified from TAA after two decades of intense research amounts to less than 600 (1). The ability to rapidly identify new CTL epitopes facilitates the development of effective immunotherapeutic strategies against cancer.

MHC molecules can be isolated from cells, and the associated peptides eluted for identification by mass spectrometry (MS). Ultimately, this approach may provide a description of the entire MHC-bound peptide repertoire; the immunopeptidome (2, 3). This is, however, a daunting task, and it is unclear whether current MS-based protocols provide the required sensitivity. Indeed, although 100,000-750,000 peptide-MHC class I complexes are expressed for each allelic product on the cell surface (for HLA-A and HLA-B loci) (3, 4), the largest HLA-ligandome identified to date contains 14,065 peptides (5). In contrast, the predicted number of different HLA class I ligands would be 352.000 using the well-renowned computer algorithm NetMHCpan, considering that on average 4.4% of all nonamers bind HLA class I (6) and that a cell contains at least $8 \times 10^6$ distinct nonamers (7). Thus, there is a very large gap between the number of confirmed and predicted HLA ligands. In addition, it is not known which fraction of the confirmed HLA ligands are actually functional epitopes and can stimulate a CTL response.

It is therefore crucial to identify additional potent CTL epitopes, in order to develop new and effective immunotherapy strategies. Consequently, methods enabling efficient identification of functional epitopes are urgently needed.

SUMMARY OF THE INVENTION

The present invention relates to CTL peptide epitopes, high-throughput methods for their identification, and their uses. In particular, the present invention relates to peptide epitopes for cancer immunotherapy and Hepatitis C Virus (HCV) vaccines. The present invention also relates to methods and systems for identifying CTL peptide epitopes.

In some embodiments, the present invention provides a method of identifying cytotoxic T cell epitopes from an antigen of interest, comprising: a) expressing at least one candidate antigen and a defined HLA molecule (e.g., HLA-A*02:01), in an antigen presenting cell, or expressing at least one candidate antigen in an antigen-presenting cell that is naturally positive for the defined HLA; b) utilizing an affinity-based algorithmic prediction to identify peptides from the candidate antigen that are predicted to bind to the defined HLA molecule (e.g., HLA-A*02:01); c) complexing each of the predicted peptides with the HLA molecule (e.g., HLA-A*02:01) to generate synthetic peptide:HLA complexes; d) contacting the antigen-presenting cells with T cells that are not tolerant to the peptide-HLA complex to induce T cell responses against the complexes; and e) contacting the synthetic peptide:HLA multimers with the T cells to directly identify epitopes that react with the antigen presenting cells.

In some embodiments, the present invention provides a method of identifying cytotoxic T cell epitopes from an antigen of interest, comprising: a) expressing at least one candidate antigen and a defined HLA molecule (e.g., HLA-A*02:01), in an antigen presenting cell, or expressing at least one candidate antigen in an antigen-presenting cell that is naturally positive for the defined HLA; b) utilizing an affinity-based algorithmic prediction to identify peptides from the candidate antigen that are predicted to bind to the defined HLA molecule (e.g., HLA-A*02:01); c) contacting the antigen-presenting cells with T cells that are not tolerant to the peptide-HLA complex to induce T cell responses against the complexes; d) complexing each of the predicted peptides with the HLA molecule (e.g., HLA-A*02:01) to generate synthetic peptide:HLA complexes; and e) contacting the synthetic peptide:HLA multimers with the T cells to directly identify T cells reactive to the predicted peptide-HLA complexes.

In some embodiments, cells that express the defined HLA molecule and the predicted peptides are used to stimulate the induced T cells to directly identify responding T cells among induced T cells by means of for instance cytokine production, upregulation of membrane markers or degranulation.

In some embodiments, the complexes are multimerized to increase binding strength (e.g., to generate HLAp multimers). In some embodiments where the peptide antigen is foreign to the T cells (e.g. HCV-derived peptides) the defined HLA molecule is further expressed by the T cells (e.g., self-HLA molecule). In some embodiments where the peptide antigen is derived from a self-protein (e.g., CD20 or myeloperoxidase), the defined HLA molecule is not expressed by the T cells (e.g., foreign HLA-molecule). Thus, in both situations, the peptide-HLA complex is recognized as foreign by the T cells as either the peptide or the HLA molecule is foreign to the T cells. In some embodiments, the candidate target proteins are screened for cell-type specific expression in normal and disease-affected cells prior to use in the epitope identification assay. In some embodiments, the complexing of peptides with HLA-molecules for subsequent generation of peptide:HLA multimers comprises UV-induced ligand exchange and multimerization. In some embodiments, the complexes are labeled.

In further embodiments, the present invention provides methods of identifying cytotoxic T cell epitopes from an antigen of interest, comprising: a) expressing at least one candidate self-antigen in an antigen presenting cell that expresses a defined HLA molecule; b) utilizing an affinity-based algorithmic prediction to identify a plurality of peptides from the candidate antigen that are predicted to bind to the defined HLA molecule to provide predicted peptides; c) synthesizing the predicted peptides and forming complexes of the synthesized predicted peptides with the defined HLA molecule to generate predicted peptide:defined HLA molecule complexes; d) contacting the antigen-presenting cells with T cells that lack expression of the defined HLA antigen and therefore are not tolerant to the predicted peptide: defined HLA molecule complexes to provide induced T cells; and e) identifying T cells reactive with the predicted peptide:defined HLA molecule complexes by contacting the induced T cells with the predicted peptide:defined HLA molecule complexes to identify T cells reactive with the complexes.

In still further embodiments, the present invention provides methods of identifying cytotoxic T cell epitopes from an antigen of interest, comprising: a) expressing at least one candidate foreign antigen in an antigen presenting cell that expresses a defined HLA molecule; b) utilizing an affinity-based algorithmic prediction to identify a plurality of peptides from the candidate antigen that are predicted to bind to the defined HLA molecule to provide predicted peptides; c) complexing the predicted peptides with the defined HLA molecule to generate peptide:defined HLA molecule complexes; d) contacting the antigen-presenting cells with T cells that are not tolerant to the peptide:defined HLA molecule complexes to induce T cell responses against the complexes in vitro; and e) identifying T cells reactive with the predicted peptide:defined HLA molecule complexes by contacting the induced T cells with the predicted peptide: defined HLA molecule complexes to identify T cells reactive with the complexes.

In some embodiments, the defined HLA molecule is naturally expressed in the antigen presenting cell. In some embodiments, the defined HLA molecule is exogenously expressed in the antigen presenting cell. In some embodiments, the defined HLA molecule is HLA-A*02:01. In some embodiments, the candidate foreign antigen is expressed by transfection of mRNA encoding the antigens. In some embodiments, the candidate foreign antigen is foreign to the T cells and the defined HLA molecule is expressed by the T cells. In some embodiments, the candidate foreign antigen is an HCV antigen. In some embodiments, the candidate foreign antigen is derived from a self-protein and the defined HLA molecule is not expressed by the T cells. In some embodiments, the candidate foreign antigen is CD20 or myeloperoxidase. In some embodiments, the candidate foreign antigen is screened for cell-type specific expression in normal and disease-affected cells prior to the expressing.

In some embodiments, the complexing comprises UV-induced ligand exchange and multimerization. In some embodiments, the complexes are labeled. In some embodiments, the identification comprises identifying reactive T cells by assaying cytokine production following stimulation of the induced T cells with the antigen presenting cells. In some embodiments, the identification comprises identifying reactive T cells by assaying upregulation of membrane markers following stimulation of the induced T cells with the antigen presenting cells. In some embodiments, the identification comprises identifying reactive T cells by assaying degranulation following stimulation of the induced T cells with the antigen presenting cells. In some embodiments, the methods further comprise the step of cloning a T-cell receptor from one of the identified T-cells and modifying T-cells isolated from a patient to express the T-cell receptor. In some embodiments, the methods further comprise administering the modified T cells to a patient who naturally expresses the defined HLA molecule.

It will be understood that the candidate foreign antigens and HLA molecules may be expressed in the antigen presenting cells by a variety of methods known in the art, including, but not limited to, transfection with RNA, transfection with DNA expression constructs, transfection with plasmid expression constructs, and transduction with viral expression constructs. In some embodiments the viral expression construct is an adenoassociated or a lentiviral vector. Electroporation and other means known in the art for introducing nucleic acids into cells may also be used for expressing the candidate foreign antigen and HLA molecules.

In some embodiments, the methods of the present invention preferably utilize predicted peptides with a specified predicted binding affinity, for example, a predicted KD of less than 500 nm, 300 nm, 200 nm, 100 nm, or preferable less than 50 nm or 20 nm or 10 nm.

Additional embodiments provide CTL epitopes identified by aforementioned methods, for use in identification of therapeutically relevant T cells and T-cell receptors.

In some embodiments, the present invention provides a method of treating cancer, comprising, isolating peripheral blood cells; and activating the T-cells (e.g., CTL), to recognize one or more epitopes (e.g., those in Tables 1 or 2 (SEQ ID Nos:1-50)) from cell-type specific self-proteins in the context of a defined foreign HLA molecule; expanding them to increase the cell numbers; and transfusing them back to the patient.

In some embodiments, the present invention provides a method of a) generating T cells by the aforementioned method; b) isolating the T-cells; c) performing T cell receptor cloning and sequence identification: and d) genetically modifying T cells isolated from a patient ex vivo to express the T cell receptor(s); and e) transfusing the modified T-cells back to the patient.

In some embodiments, T-cells recognizing one of the epitopes in Tables 1 or 2 (SEQ ID Nos:1-50) are expanded by contacting them with a synthetic peptide of Tables 1 or 2 (SEQ ID Nos:1-50) in cell culture when complexed with the defined HLA molecule expressed on antigen-presenting cells. In some embodiments, one or more cytokine (e.g., IL-2) is administered with the activated T-cells.

In some embodiments, the present invention provides methods of treating cancer in a subject who naturally expresses a defined HLA molecule, comprising: a) isolating peripheral blood comprising T-cells from a donor lacking the HLA molecule, b) activating the T-cells to recognize one or more epitopes identified by the methods described above by contacting the T-cells with a peptide antigen complexed with the HLA molecule expressed on antigen-presenting cells; c) expanding the T-cells to provide an expanded population of T cells followed by isolation of T cells in the expanded population of T-cells that recognize the peptide-HLA complex; and d) administering the isolated T-cells to the patient. In some embodiments, the T-cells are CTL. In some embodiments, the peptide antigen is selected from the group consisting of SEQ ID Nos:1-50 and a peptide from a cell-type specific self protein. In some embodiments, one or more cytokines are administered concurrently with the activated T-cell. In some embodiments, the cytokine in IL-2. In some embodiments, a peptide selected from the group consisting of SEQ ID NOs:1-50 is administered with the activated T-cells. In some embodiments, the isolation comprises contacting the T cells with soluble multimers of the peptide antigen complexed with the HLA molecule.

In some embodiments, the T cells or T cell receptors of the present invention are used in combination with other treatment modalities, including but not limited to small molecule drugs (chemotherapy agents), antibodies and vaccines. The combination therapy may be either concurrent or sequential.

In some embodiments, the present invention provides a method of treating infection by a microorganism (e.g. HCV infection), comprising: a) isolating peripheral blood cells; b) activating T-cells in the blood cells (e.g., CTL) to recognize one or more disease specific epitopes (e.g., those in Table 3 (SEQ ID Nos:51-70)) using the aforementioned method; c) expanding T-cells recognizing the epitope to increase the cell numbers; and d) transfusing them back to the patient. In some embodiments, the T cells recognizing the epitope are isolated for T cell receptor cloning and sequence identification, and one or more of the T cell receptors are used to genetically modify patient T cells outside the patient to express the T cell receptor(s), and subsequently transfused back to the patient.

In some embodiments, the present invention provides methods of treating infection by a microorganism in a subject naturally expressing a defined HLA molecule, comprising: a) isolating peripheral blood comprising T-cells from the subject, b) activating the T-cells to recognize one or more epitopes by contacting the T-cells with a peptide antigen complexed with the HLA molecule expressed by antigen-presenting cells; c) expanding the T-cells to increase the number of cells; and d) administering the activated T-cells to the patient. In some embodiments, the T-cells are CTL. In some embodiments, the peptide antigen is selected from the group consisting of SEQ ID NOs:51-70. In some embodiments, the microorganism is HCV. In some embodiments, one or more cytokines are administered concurrently with the activated T-cell. In some embodiments, the cytokine is IL-2. In some embodiments, a peptide selected from the group consisting of SEQ ID NOs:51-70 is administered with the activated T-cells.

Embodiments of the present invention provide a vaccine composition comprising a peptide comprising one or more immunogens selected from the group consisting of the peptides described in Table 3. In some embodiments, the immunogen is covalently bound to a carrier protein (e.g., cholera toxin, *pseudomonas* exotoxin A, toxoids, virus like particles, tetanus toxin/toxoid, diphtheria toxin/toxoid or hepatitis B surface protein). In some embodiments, the carrier protein is a sterile pharmaceutically acceptable carrier protein. In some embodiments, the vaccine composition further comprises an adjuvant.

Additional embodiments provide a method of inducing an immune response, comprising administering a vaccine composition described herein to a subject under conditions such that the subject generates an immune response (e.g., T-cell mediated immune response) to a viral target, including but not limited to the HCV protein NS3 and/or Core antigens.

In some embodiments, the immune response treats HCV infection in the subject.

Further embodiments of the present invention provide a kit comprising the vaccine composition described herein. In some embodiments, the kit further comprises a device for administration of the vaccine. In some embodiments, the kit further comprises one or more additional components (e.g., including but not limited to, sanitation components, temperature control components, adjuvants, a physiologically tolerable buffer, or instructions for using the vaccine composition).

Additional embodiments of the invention are described herein.

DEFINITIONS

Figure 1:
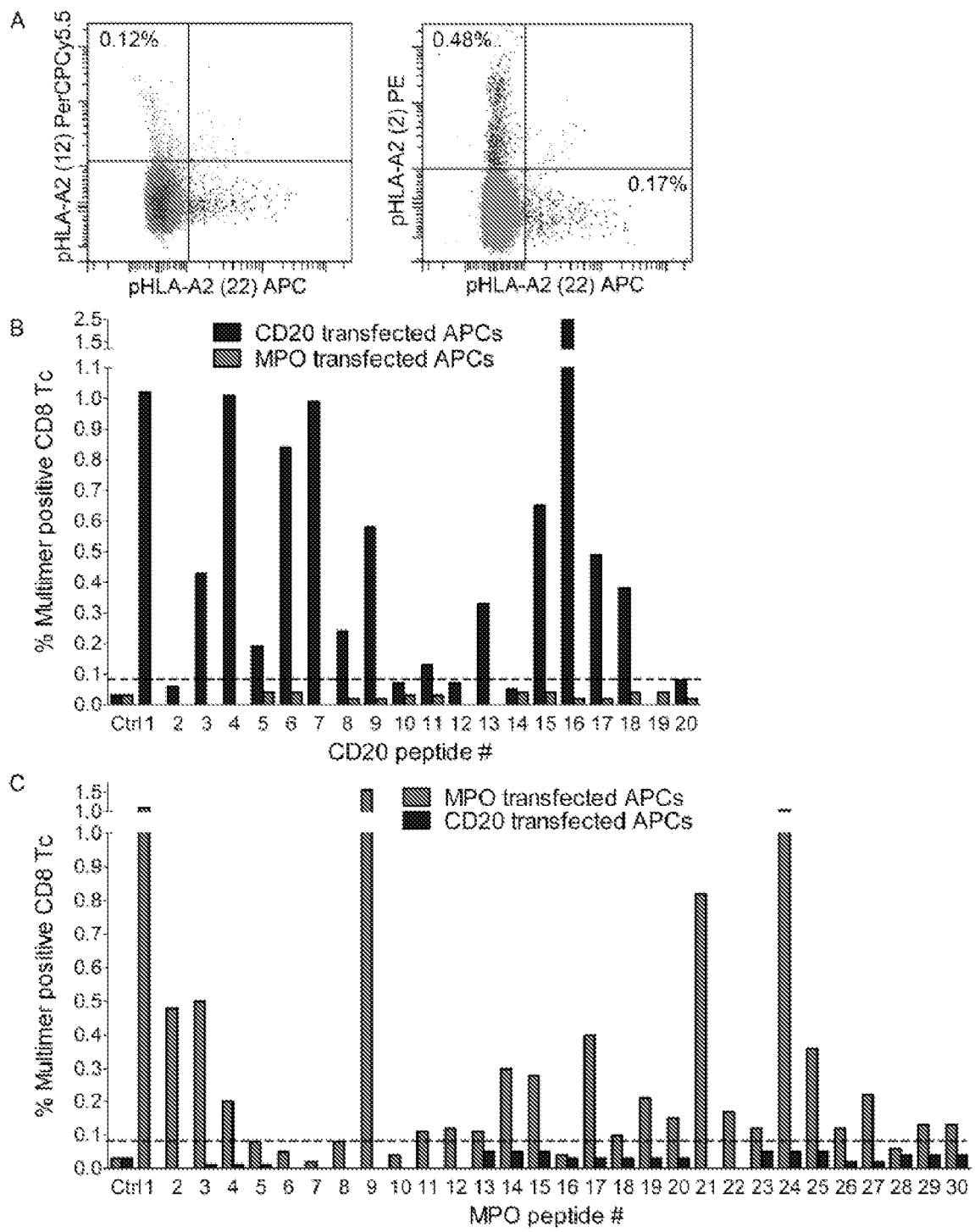
FIG. 1. Allo-restricted CTLs recognize 37/50 algorithm-predicted epitopes from the differentiation antigens CD20 and MPO. (A-C) T cells from HLA-A2neg donors were stimulated with HLA-A2-transfected APCs (moDCs for priming and EBV-LCLs for re-stimulation). The APCs were co-transfected with mRNA transcripts encoding full-length CD20 or MPO, respectively. (A) T cells were primed with APCs transfected with MPO. The dot plots are gated on viable CD8pos T cells and show staining with color-coded pHLA-multimers complexed with three different MPO peptides; numbers in parenthesis indicate peptide numbers as shown in (C). Flow cytometric analysis of cells staining positively for multimers conjugated to PE, APC or PerCP-Cy5.5 is shown as red, blue or green dots, respectively. (B,C) T cells were primed with APCs transfected with CD20 (blue bars) or MPO (red bars). Bars show frequencies of cells staining positively with pHLA-A2 multimers with indicated peptides from CD20 (B) or MPO (C) among viable CD8pos T cells. Control multimers (ctrl) were complexed with two irrelevant peptides (MART-1 (ELAGIGILTV) (SEQ ID NO:73)) or CMV (NLVPMVATV) (SEQ ID NO:74)) and mixed. Results shown are representative of 2 (CD20) or 4 (MPO) experiments. Horizontal dashed lines indicate cut-off.

To facilitate understanding of the invention, a number of terms are defined below.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "peptide" refers to a polymer of two or more amino acids joined via peptide bonds or modified peptide bonds. As used herein, the term "dipeptides" refers to a polymer of two amino acids joined via a peptide or modified peptide bond.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

As used herein, the term "purified" or "to purify" refers to the removal of contaminants from a sample. For example, antigens are purified by removal of contaminating proteins. The removal of contaminants results in an increase in the percent of antigen (e.g., antigen of the present invention) in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants An antigenic determinant may compete with the intact antigen (i.e., the "immunogen" used to elicit the immune response) for binding to an antibody.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "microorganism" refers to any species or type of microorganism, including but not limited to, bacteria, viruses, archaea, fungi, protozoans, *mycoplasma*, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, *mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a bacterium)), may be responsive to environmental factors (e.g., malnutrition, industrial hazards, and/or climate), may be responsive to an inherent defect of the organism (e.g., genetic anomalies) or to combinations of these and other factors.

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present invention (e.g., comprising nanoemulsion inactivated RSV) are administered with one or more adjuvants (e.g., to skew the immune response towards a Th1 or Th2 type response).

As used herein, the term "carrier protein" references to a molecule that interacts (e.g., via covalent attachment) to an antigen or immunogen. In some embodiments, carrier proteins enhance the presentation of antigens to the immune system. In some embodiments, the resulting complex engages the T cell arm of the immune response, resulting in higher levels of antibodies and cell response. In some embodiments, carrier proteins are sterile and pharmaceutically acceptable.

As used herein, the term "under conditions such that the subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In some embodiments, immunogens elicit immunity against the immunogen (e.g., microorganism (e.g., pathogen or a pathogen product)).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention relates to CTL peptide epitopes, high-throughput methods for their identification, and their uses. In particular, the present invention relates to peptide epitopes for cancer immunotherapy and Hepatitis C Virus vaccines. The present invention also relates to methods and systems for identifying CTL peptide epitopes.

Leukemia/lymphoma are treated with a variety of therapeutic modalities, including chemotherapy, monoclonal antibodies and/or T cell-based immunotherapy, in the form of allogeneic hematopoietic stem cell transplantation (AHSCT). Although many patients respond to AHSCT, only few patients are eligible for this therapy due to its high treatment-related morbidity and mortality. Thus, for large fractions of these patients there is no cure, and a large unmet need for improved therapeutic options.

Fifty-eighty % of patients fail to develop an appropriate immune response to acute infection with Hepatitis C Virus and develop chronic infection, which might lead to subsequent liver damage and liver cancer. There is currently no effective prophylactic vaccine for Hepatitis C Virus, and large fractions of patients with chronic infection are not cured by available treatment. There is thus a large unmet need for development of more effective vaccines/immunotherapy strategies against Hepatitis C Virus infection.

Self-TAA are the main targets in immunotherapy of cancer today. However, only 600 CTL epitopes have been discovered thus far in spite of 20 years of research, of which only 250 are from non-melanoma antigens. The main reason is that T cell responses to various epitopes have been studied in patients, who are tolerized against self-TAA presented on self-HLA. The approach described herein provides a multitude of novel targets from self-TAA discovered with high sensitivity, which is a huge improvement relative to approaches used today. Thus, in one study of two proteins we rapidly identified 37 CTL epitopes.

Although immunogenic epitopes in Hepatitis C Virus have been extensively studied, 5 novel epitopes were discovered in the NS3 antigen, and in addition a large number of the known epitopes were confirmed.

Accordingly, embodiments of the present disclosure provide novel peptide epitopes to CD20 and MPO that provide targets for cancer immunotherapy of these patients and epitopes to NS3 useful in the generation of an immune response to Hepatitis C virus (HCV).

Today, the discovery of CTL epitopes for use in vaccination and immunotherapy of cancer (infection) is done by studying cells from patients with cancer (infection). However, all studies depending on patient cells for epitope discovery are limited by tolerance to self and previous immunization history of the individual. In contrast, the strategy presented here took advantage of induction of responses in T-cell repertoires from antigen-inexperienced, non-tolerized individuals. This indicates that the use of self-tolerant T-cell repertoires, rather than poor peptide presentation, is the reason why few cancer epitopes have been previously identified.

CTLs recognize a complex between a peptide, called cancer antigen peptide, and a major histocompatibility complex class I antigen (MHC class I antigen, also referred to as HLA antigen) through the T cell receptors (TCRs), and thereby attacking autologous tumor cells.

In some embodiments, the present invention provides a cancer vaccine that activates CTL. In some embodiments cancer immunotherapy is ex vivo T-cell mediated immunotherapy (See e.g., Overwijk et al., J Exp Med. 2003 Aug. 18; 198(4): 569-580 and Rosenberg et al., Nat Med. 2004 September; 10(9): 909-915; each of which is herein incorporated by reference in its entirety). In some embodiments, ex vivo T-cell medicated cancer vaccines or immunotherapy agents are generated by isolation of either allogenic or autologous immune cells, enriching or activating them outside the body (e.g., by contacting them with a peptide of Table 1) and transfusing them back to the patient. The injected immune cells are highly cytotoxic to the cancer cells expressing a particular epitope, targeting cancer cells (See e.g., Maher et al, Br J Cancer. 2004 Aug. 31; 91(5): 817-821; herein incorporated by reference in its entirety). In some embodiments, activated T-cells (e.g., CTL) are administered along with one or more cytokine (e.g., IL-2).

In some embodiments, cancer therapy combines ex vivo T-cell stimulation and a cancer vaccine (e.g., comprising a peptide described in Table 1).

In some embodiments, cell-based immunotherapy is conducted in vivo by administering a peptide described herein along with an agent that stimulates CTLs (e.g., cytokines such as Interleukins). The peptides described herein have a CTL-inducing ability and such induced CTLs can exert the anti-cancer activity through cytotoxic action or production of lymphokines. The peptides described herein can be used as an active ingredient of cancer vaccine for treating or preventing cancer. Thus, the present invention provides cancer vaccine (pharmaceutical composition as cancer vaccine) comprising as an active ingredient a peptide (e.g., those in Table 1). When cancer vaccine of the present invention is administered to a patient, the peptide is presented to antigen-presenting cells. Then, CTLs specifically recognizing the presented HLA-antigen complex proliferate and destroy the cancer cells, whereby the treatment or prevention of cancer becomes possible. The cancer vaccine of the present invention can be used in the prevention or treatment of a variety of cancers (e.g., myeloid leukemia or a B-lymphoid malignancy).

Thus, in another embodiment, the present invention provides a method for treatment or prevention of cancer, which comprises administering an effective amount of cancer vaccine of the present invention to a patient in need thereof.

The cancer vaccine comprising as an active ingredient a peptide of the present invention may contain a single CTL epitope (e.g., those described in Table 1) or an epitope peptide wherein a peptide is ligated with other peptide(s) (CTL epitope, helper epitope, etc.) as an active ingredient. In some embodiments, multiple peptides are utilized.

The cancer vaccine comprising as an active ingredient a peptide of the present invention may be administered together with a pharmaceutically acceptable carrier, for example, an appropriate adjuvant, or in the form of particles so that the cellular immunity can be established effectively. As an adjuvant, those described in a literature (Clin. Microbiol. Rev., 7:277-289, 1994), and the like are applicable. Concrete examples include microorganism-derived components, cytokines, plant-derived components, marine organism-derived components, mineral gels such as aluminium hydroxide, surfactants such as lysolecithin and Pluronic polyols, polyanions, peptides, oil emulsion (emulsion preparations) and the like. Liposomal preparations, particulate preparations in which the ingredient is bound to beads having a diameter of several μm, preparations in which the ingredient is attached to lipids, and the like, are also contemplated.

Administration may be achieved, for example, intradermally, subcutaneously, intramuscularly, or intravenously. Although the dosage of the peptide of the present invention in the formulation may be adjusted as appropriate depending on the disease to be treated, the age and the body weight of patient, it is usually within the range of 0.0001 mg-1000 mg, preferably 0.001 mg-1000 mg, more preferably 0.1 mg-10 mg, which can be preferably administered once in every several days to every several months.

In some embodiments, the HCV peptide epitopes described herein are used to generate vaccines. In some embodiments, immunocarriers (e.g., carrier proteins) are attached to immunogens. In some embodiments, carrier proteins are covalently linked to an antigen or immunogen. Exemplary carrier proteins include, but are not limited to, cholera toxin, *pseudomonas* exotoxin A, toxoids, virus like particles, tetanus toxin/toxoid, diphtheria toxin/toxoid and hepatitis B surface protein. Additional carrier proteins are known to those of skill in the art.

An effective amount of the present vaccine is one in which a sufficient immunological response to the vaccine is raised to protect a subject exposed to HCV or generate a cancer specific immune response. Preferably, the subject is protected to an extent in which from one to all of the adverse physiological symptoms or effects of the disease to be prevented are found to be significantly reduced.

In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatized polysaccharides, or polyphosphazenes.

In general, an immune response is generated to an antigen through the interaction of the antigen with the cells of the immune system Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising an immunogen. However, in other embodiments, the present invention provides a method of stimulating a Th2-type immune response in a subject (e.g., if balancing of a T cell mediated response is desired) comprising administering to a subject a composition comprising an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. Coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising an immunogen of the present invention.

Additional examples of adjuvants that find use in the present invention include poly(dicarboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising an immunogen, or, the adjuvant may be formulated with carriers, for example liposomes, or metallic salts (e.g., aluminium salts (e.g., aluminium hydroxide)) prior to combining with or co-administration with a composition.

In some embodiments, a composition comprising an immunogen comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising an immunogen comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising an immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising an immunogen of the present invention can be used therapeutically (e.g., to enhance an immune response) or as a prophylactic (e.g., for immunization (e.g., to prevent signs or symptoms of disease)). A composition comprising an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this invention. Compositions of the present invention may also be administered via the oral route. Under these circumstances, a composition comprising an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising an immunogen is administered to a mucosal surface of a subject in either a priming or boosting vaccination regime. Alternatively, in some embodiments, the composition is administered systemically in either a priming or boosting vaccination regime. In some embodiments, a composition comprising an immunogen is administered to a subject in a priming vaccination regimen via mucosal administration and a boosting regimen via systemic administration. In some embodiments, a composition comprising an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising an immunogen of the present invention may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., E. coli). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, transdermal, intranasal, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins. Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product. The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the immunogen or other components of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, vaccine compositions are co-administered with one or more other agents useful in treating cancer or infection by HCV. There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e g, aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a vaccine composition comprising an immunogen with one or more additional active and/or immunostimulatory agents (e.g., a composition comprising a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising an immunogen is administered to a subject via more than one route. For example, a subject that would benefit from having a protective immune response (e g, immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of the composition) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a vaccine composition of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of a nanemulsion and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

In some embodiments, the present invention provides a platform (e.g., systems and methods) for identifying CTL epitopes. Embodiments of the present invention utilize T cell repertoires that have not been rendered tolerant as tools for efficient and sensitive detection of the epitopes. More precisely, for discovery of epitopes from self-TAA by non-tolerant T cells, the self-TAA are presented on HLA-molecules for which the T cell donor is negative. Thus, the self-TAA are presented on antigen-presenting cells expressing HLA-A2, whereas the T cells are HLA-A2 negative. T cells recognizing peptides presented on foreign HLA are termed allo-reactive, or allo-restricted.

In some embodiments, the method comprises the following steps: (1) Candidate target proteins are screened for cell-type specific expression in normal and malignant hematopoietic cells (GeneSapiens.org). (2) Selected target proteins, and HLA-A*02:01, are cloned and recombined into a vector for in vitro production of mRNA encoding full-length protein. (3) Monocyte-derived dendritic cells from HLA-A2neg donors are transfected with the mRNA, and subsequently co-cultured with autologous, non-adherent peripheral blood mononuclear cells. The cultures may be re-stimulated with EBV-LCLs transfected with mRNA encoding the target protein and HLA-A2 on days 12, and 19 (not shown, and optional). (4) Selected targets are subjected to affinity-based algorithmic prediction of HLA-A*02:01-restricted peptides (cbs.dtu.dk/services/NetMHC/) and those predicted to bind with the highest affinities are synthesized. (5) These peptides are complexed with HLA-A*02:01 monomers by UV-induced ligand exchange, followed by multimerization using streptavidin (SA) conjugated to, e.g., PE, APC or PerCP-Cy5.5, respectively. (6) By end of culture (e.g. days 12, 19 or 26), CD8 positive T cells reactive to different epitopes are detected by flow cytometric measurements of combinations of fluorescently labeled pHLA-A2 multimers.

For discovery of epitopes from foreign antigens, for example Hepatitis C Virus (HCV), donors that are seronegative for HCV and have not undergone infection with the virus, are used, as the T cell repertoires from such donors are not rendered tolerant to the virus. For discovery of epitopes in foreign antigens, for instance proteins derived from Hepatitis C Virus, dendritic cells and T cells are harvested from the same HLA-A2 positive donor, otherwise the procedure is the same as described above.

EXPERIMENTAL

The following examples are provided in order to demonstrate and further illustrate certain preferred embodiments and aspects of the present invention and are not to be construed as limiting the scope thereof.

Example 1

Materials and Methods

Healthy Donors and Cell Lines

This study was approved by the Regional Ethics Committee and performed in accordance with the declaration of Helsinki. Healthy donors were HLA-typed by standard molecular techniques.

THP-1 and JVM-2 cells were obtained from Deutsche Sammlung von Mikroorganismen and Zellkulturen. The following cell lines were kind gifts: SupT1 cells from M. Pule (University College London, UK); K562 (CCL 243) cell line from John Torgils Vaage; primary adipose tissue-derived mesenchymal stem cells (MSC) from J. Brinchmann's laboratory (Institute of Immunology, Oslo University Hospital (OUS) Rikshospitalet); HaCaT keratinocyte cell line from Dr. F. Jahnsen (Dept of Pathology, OUS Rikshospitalet); colorectal carcinoma cell line HCT-116 (CCL-247), colorectal adenocarcinoma cell line Caco-2 (HTB-37), hepatocellular carcinoma cell line Hep G2 (HB-8065) and lung adenocarcinoma cell line NCI-H522 (CRL-5810) from Ragnhild A. Lothe and Guro E. Lind (Dept of Cancer Prevention); FM81 and T2 cells from Else Marit Inderberg Suso (Dept of Immunology) and HeLa cells from Andreas Brech (Dept of Biochemistry), all at OUS Radiumhospitalet. Platinum-E (Plat-E) retroviral packaging cell line (referred to as HEK) (Cell Biolabs, San Diego, Calif., USA) and HeLa cells were maintained in DMEM (Invitrogen); MSC, HaCaT and HCT-116 were grown in D-MEM/F12 (Sigma); Caco-2 and Hep G2 in EMEM (ATCC®), all with 10% FCS and penicillin/streptomycin (P/S). The other cell lines were cultured in RPMI 1640 (Gibco), with 10% FCS and P/S.

Prediction of HLA-A*02:01 Specific Peptides from Target Proteins

Protein sequences were obtained from NCBI Entrez engine. Prediction of HLA-A*02:01-binding peptides from target proteins was performed using the algorithms NetMHCpan 2.2 (6) for MPO, or NetMHC 3.2 (40) for CD20 and HCV. Peptides with an IC50 score of <500 nM were considered potential HLA-A2 binders, and are listed in Table 1.

Generation of Peptide-HLA Complexes

All predicted peptides, and control peptides ELAGIGILTV (SEQ ID NO:73) (MART-1) and NLVPMVATV (SEQ ID NO:75) (CMV), were synthesized by Proimmune Ltd. (Oxford, UK) or GenScript Inc. (USA). Synthesis of conditional HLA-A2 ligands containing a UV-sensitive peptide was performed as described in (13, 41). For generation of pMHC multimers, fluorochrome-streptavidin (SA) conjugates were generated as described in (13), with phycoerythrin (PE), allophycocyanin (APC) (BD Biosciences), or Peridinin-chlorophyll protein-Cy5.5 (PerCP-Cy5.5) (Ebiosciences). HLA-B*08:01 and HLA-B*07:02-restricted pentamers were from ProImmune Ltd. (Oxford, UK).

Plasmid Constructs, mRNA/DNA-Transfection and Retroviral Transduction

MPO was amplified from reverse-transcribed mRNA from HL-60 cells with Pfx (Invitrogen) using the primers: 5'-caccATGGGGGTTCCCTTCTTC-3' (SEQ ID NO:71) and 5'-TCAGGCGTAGTCGGGCACGTCGTAGGGGTAG-GAGGCTTCCCTCCAGGAAG-3' (SEQ ID NO:72), subcloned into pENTR/D-TOPO (Invitrogen) and recombined into the Gateway compatible pCIpA102-G vector for mRNA production following sequencing (42). The CD20 mRNA expression construct was reported in (23). The mRNA encoding HLA-A*02:01 or target proteins was generated as described in (8), and used to transfect moDCs, EBV-LCL, HaCaT, or K562 cells by electroporation (1250 V/cm for 3 ms (moDCs, HaCaT), 2 ms (K562) and 1 ms (EBV-LCL), respectively) with a BTX ECM 830 square wave electroporator (BTX, Harvard Apparatus, Holliston, Mass., USA). HEK and HeLa cells were transfected with DNA encoding HLA-A2 and MPO or CD20 using FuGENE-6 (Roche, Basel, Switzerland), following the manufacturer's protocol. Retroviral particles were produced and transduced as described in (42). HCV core and NS3 genes were synthesized by GeneArt (Invitrogen) and inserted into a Gateway compatible vector (pENT221) and subsequently recombined with pCIpA102-G. A Gateway compatible version of pMP71 was used to express MPO and/or HLA-A*02:01 in SupT1, and the MART-1 (DMFS) TcR in primary T cells (construct derived from pMSGV-DMFS_2A, a kind gift from R. Morgan (NIH, Bethesda, USA)).

Induction of Multimer Reactive T Cells Restricted by Allogeneic HLA

Mature monocyte-derived dendritic cells (moDC) were generated as described in (8) from HLA-A*02:01neg donors. One hour following mRNA-transfection, cells were combined with thawed, autologous non-adherent PBMC and cultured as described in (8, 23). Cells were re-stimulated day 12 and 19 with irradiated (25 Gy) HLA-A*02:01pos EBV-LCL transfected 4 hrs earlier with mRNA encoding the target protein, in X-vivo 20 (BioWhittaker, Lonza, Walkersville, Md., USA) with 5% pooled human serum (Trina Bioreactives AG, Nänikon) and with IL-2 supplemented at 10 U/ml on day 14 (R&D systems, USA).

Multimer Staining, Sorting and Expansion of Multimer Reactive CTL Lines

On day 26, co-cultures were stained with the succinimidyl ester dye Pacific Blue (Invitrogen Molecular Probes, USA) for live/dead cell discrimination at a final concentration of 0.1 ug/mL for 10 min at 37° C. in PBS. Two µl of 1-3 pHLA-A*02:01 tetramer(s) (in-house), or pentamers of HLA-B*07:02 or HLA-B*08:01 (Proimmune), were added for 15 min at RT to stain 1×106 co-cultured cells, followed by anti-CD8. Sorting was performed using FACS Aria or FACS Vantage SE Cell sorters (BD Biosciences, San Jose, Calif., USA). Sorted, tetramer positive cells were expanded in the presence of irradiated allogeneic PBMC in X-Vivo 20 medium with 5% pooled human serum, IL-2 (50 U/ml, R&D systems, USA), IL-15 (2 ng/ml, Peprotech EC Ltd, USA) and PHA (1 µg/ml, Remel) for 3-4 weeks.

Antibodies and Flow Cytometry

Cells were labelled with the following antibodies, in-house conjugated to Alexa Fluor 647 or Atto 488: anti-CD8 (RPA-T8), -CD107a (H4A3), -CD107b (H4B4) (all from BD Biosciences), and -HLA-A2 (BB7.2; AbD Serotec), or -CD4FITC, -MPO-PE (MPO-7; Dako, Denmark), -CD14PerCP-Cy5.5, -IFN-γPE, CD8PerCP-Cy5.5 or CD8Pacific Blue (SKI, Ebiosciences, USA). Cells were analyzed on FACS LSR II and data analysis performed with FACS DiVa (both from BD Biosciences) or FlowJo softwares (Tree Star Inc., Ashland, Oreg., USA). Functional T cell responses were measured as mobilization of CD107a/b (degranulation) and production of IFN-γ by flow cytometry, as described in (23), following co-culture with various target cells that were DNA-transfected 48 h earlier, mRNA-transfected 4-10 h earlier, or peptide-loaded (10 ug/ml for 4 h, followed by washing). CD4pos T cells were isolated using a CD4 positive isolation kit (Dynal Biotech, Norway), whereas monocytes were isolated by elutriation centrifugation.

Results

Detection of 36 Novel Epitopes in the Tumor-Associated Antigens CD20 and MPO by High-Throughput Induction of Allo-Restricted CTLs It was contemplated that T-cell repertoires that had not been rendered tolerant would allow efficient and sensitive assessment of the immunopeptidome. This was tested in a setting where peptide presentation of self-antigens by foreign HLA was induced using mRNA transfection of full-length target proteins. Monocyte-derived DCs from HLA-A2neg donors were transfected with HLA-A2, which we have demonstrated is an efficient strategy for peptide presentation on allogeneic HLA (8). The moDCs were co-transfected with mRNA encoding full-length CD20 or MPO, representing leukemia-associated antigens with an expression pattern confirmed to be highly restricted to normal and malignant hematopoietic cells across 10,000 samples (genesapiens.org). Autologous CD8pos T cells that had been co-cultured with engineered moDCs were labelled with a panel of color-coded peptide-HLA-A2 (pHLA) multimers containing peptides from CD20 or MPO that were predicted to bind HLA-A*02:01 (FIG. 1). A total of 50 peptides, ranked as strong to intermediate binders (<500 nM) (Table S1), were synthesized and used to generate pHLA multimers for T cell staining (FIG. 1A). pHLA multimer staining revealed that co-culture of T cells with CD20-transfected moDCs resulted in generation of T cells reactive with the majority of the 20 peptides from CD20 (FIG. 1B). Specificity of this interaction was shown by the fact that these peptides were not recognized by T cells primed by MPO-transfected DCs (FIG. 1B). Vice versa, T cells primed by MPO-transfected cells recognized the majority of the peptides from MPO (FIG. 1C), whereas these MPO peptides were not recognized by the cells primed with CD20-transfected DCs (FIG. 1C). HLA multimers containing peptides from irrelevant antigens (MART-1 and CMV) were not recognized by any of the T cells in the two culture conditions (FIG. 1B-C, Ctrl).

In summary, the approach resulted in detection of 14/20 of the predicted CD20 epitopes, and 23/30 predicted MPO epitopes. Of the 37 identified epitopes, 36 were novel. The generated CTLs reacted only with relevant pHLA multimers and not with a large number of irrelevant peptides, indicating the specific induction of these reactivities exclusively in the presence of the relevant antigen.

Allo-Restricted CTL Lines Recognize Peptides Presented on Leukemic and Non-Malignant Hematopoietic Cells Endogenously Expressing CD20 or MPO, and are Highly Peptide- and HLA Specific Dendritic cells are the most effective antigen-presenting cells known. Thus, it was investigated whether transfected cells present peptides that are not found on HLA molecules on leukemic cells. To assess whether the epitope repertoire was equally broad on cells endogenously expressing these target proteins, we randomly selected 13 out of the 37 multimer-reactive CTL populations for sorting, expansion of CTL lines and functional testing. The CTL lines were tested for reactivity against a panel of up to 15 HLA-A2pos target cells that were positive or negative for CD20 and/or MPO, respectively.

Figure 2:
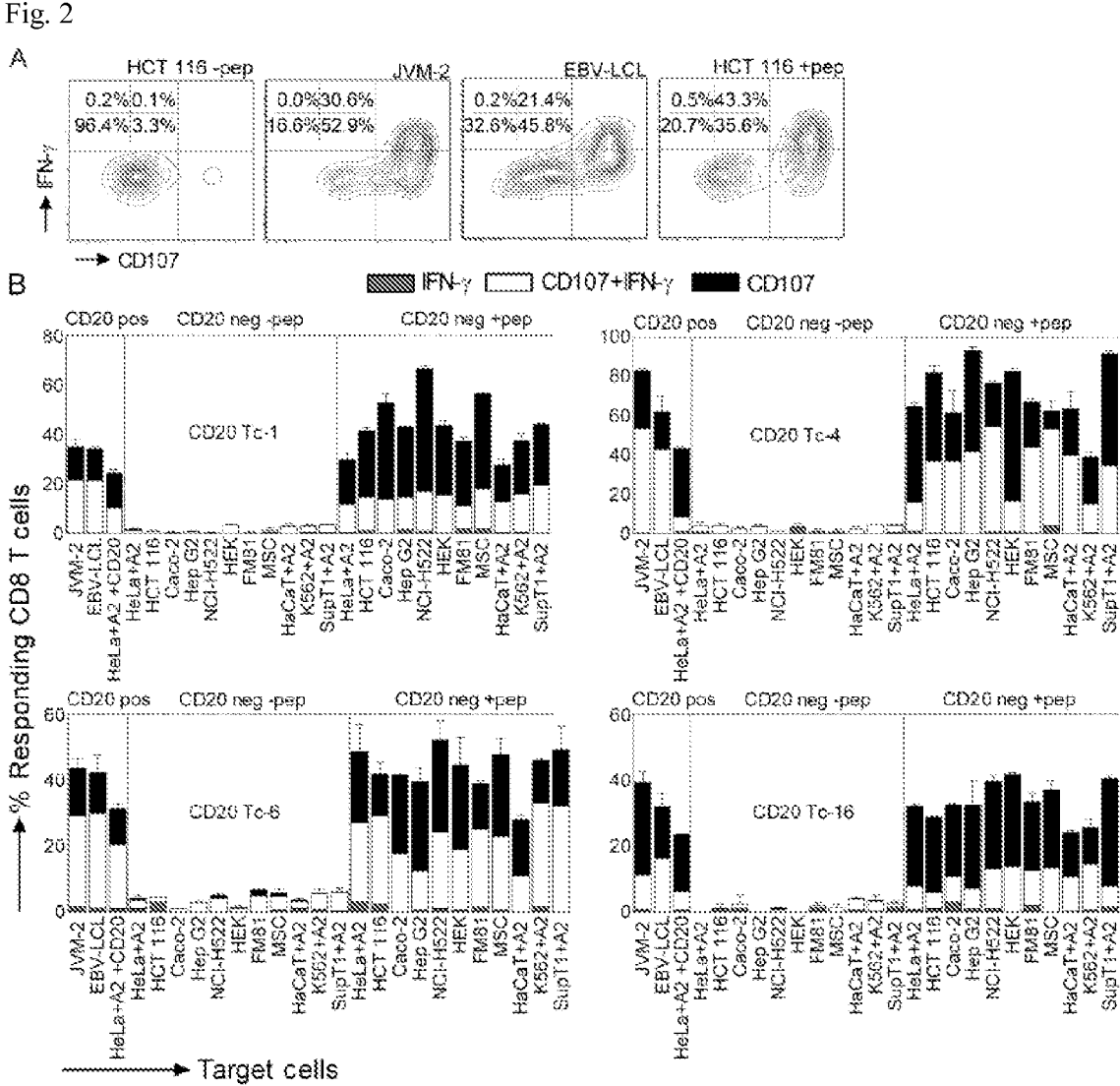
FIG. 2. Allo-restricted T cells reactive with CD20-derived epitopes respond specifically and strongly to HLA-A2posCD20pos target cells. CTLs reactive with individual CD20-HLA-A2 multimers (designated by the number of the peptide they recognized, see FIG. 1), were sorted and expanded into cell lines. The cells were co-cultured for 5 h with indicated target cells at E:T ratios of 1:2. (A) Flow cytometric analysis showing percentage of CD8posHLA-A2neg cells expressing CD107a/b (indicative of degranulation) and producing IFN-γ in cell line #4 (Tc-4) when co-cultured with indicated target cells. (B) The bars show frequencies of CD107a/b and/or IFN-γ positive events among CD8pos T cells when indicated CTL line (CD20 Tc-1, 4, 6, 16) was co-cultured with indicated target cell (x-axis). All target cells were HLA-A2pos, either naturally or by genetic introduction (+A2), as indicated. They were grouped into those expressing CD20, either naturally (JVM-2, EBV-LCLs) or by genetic modification (HeLa+A2+CD20), or into CD20 neg target cells that were peptide loaded (+pep) or not (−pep). Target cells were excluded from flow cytometric analysis by staining with anti-HLA-A2. Error bars indicate SD of duplicates. All CTL lines were tested in separate experiments.
Figure 5:
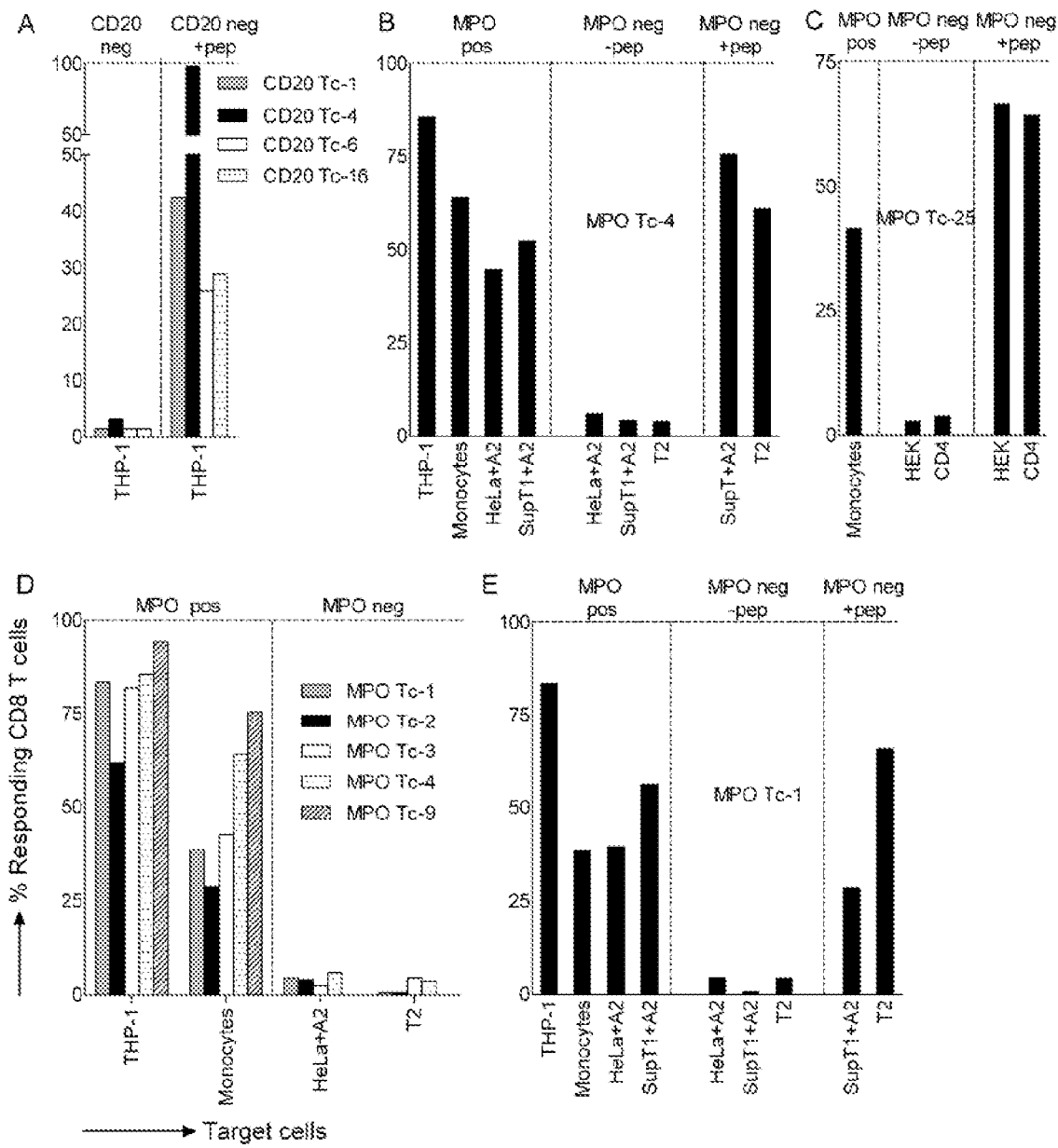
FIG. 5. CTL lines recognizing CD20 or MPO-derived peptides respond strongly and specifically to HLA-A2pos antigen positive target cells. Assays were performed as described in FIG. 2, except that only degranulation responses were measured. The bars show frequencies of CD107a/b positive cells of CD8pos cells when indicated CTL line was co-cultured with indicated target cells (x-axis). (A) All four CD20-reactive CTL lines shown in FIG. 2 were tested for reactivity against THP-1 cells in the absence or presence (+pep) of loading with relevant peptide. (B-E) CTLs reactive to MPO peptides #4 (B) and #25 (C) from the same donor as used in FIG. 3, or from an additional donor reactive to peptides #1, #2, #3, #4 or #9 (D,E), were tested for degranulation in response to the indicated target cells (x-axis). All target cells expressed HLA-A2, either naturally or induced (+A2), as indicated, and were grouped into target cells expressing MPO, either naturally (THP-1, monocytes) or induced (HeLa+A2+MPO, SupT1+A2+MPO), and into antigen negative target cells loaded (+pep) or not (−pep) with relevant peptide. The results in A are representative of two experiments performed.

The CTL lines reactive to four different peptides from CD20 responded strongly by degranulation and interferon (IFN)-γ production to HLA-A2pos target cells endogenously expressing CD20 (FIG. 2A,B). These included EBV-transformed lymphoblastoid cell lines (EBV-LCLs), the B-prolymphocytic leukemia cell line JVM-2, but also CD20/HLA-A2-transfected HeLa cells (FIG. 2A,B). Reactivity was also tested against a variety of cell lines of different histologies that expressed HLA-A2, but not CD20, such as colon carcinoma (HCT-116, Caco-2), liver carcinoma (Hep G2), lung adenocarcinoma (NCI-H522), keratinocytes (HaCaT), malignant melanoma (FM81), human embryonic kidney (HEK), cervix adenocarcinoma (HeLa), T cell lymphoblastic lymphoma (SupT1), chronic myelogeneous leukemia (K562) and mesenchymal stem cells (MSC) (FIG. 2B). No or only very low reactivity was seen against this wide range of targets (FIG. 2A,B). However, responses against these target cells were again observed when the cells were loaded externally with the relevant peptide. Furthermore, the four CD20-reactive CTL lines did not respond to the acute myelomonocytic leukemia cell line THP-1, unless loaded with relevant CD20 peptides (FIG. 5A).

Figure 3:
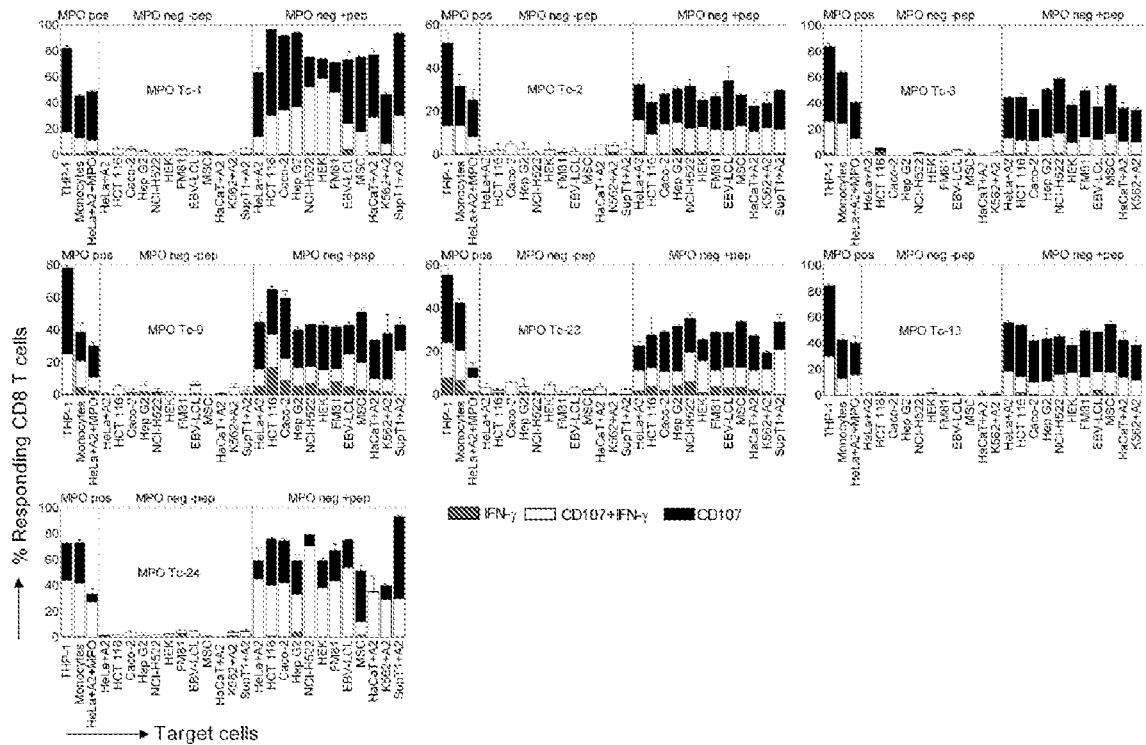
FIG. 3. Allo-restricted T cells reactive with MPO-derived epitopes respond specifically and strongly to HLA-A2posMPOpos target cells. Assays were performed as described in FIG. 2. The bars show frequencies of CD107a/b and/or IFN-γ positive events among CD8posHLA-A2neg T cells when indicated CTL line (MPO Tc-1, 2, 3, 9, 13, 23, 24) was co-cultured with indicated target cell (x-axis). All target cells were HLA-A2pos, either naturally or by genetic modification (+A2), as indicated. They were grouped into those expressing MPO, either naturally (THP-1, monocytes) or induced (HeLa+A2+MPO), or into MPO negative target cells that were peptide loaded (+pep) or not (−pep). SupT1 cells were not available when performing the experiments for Tc-3 and -13. Target cells were excluded from flow cytometric analysis by staining with anti-HLA-A2. Error bars indicate SD of duplicates. All CTL lines were tested in separate experiments.

Similarly, CTL lines reactive to 7 different peptides from MPO responded strongly by degranulation and IFN-γ production to HLA-A2pos target cells that endogenously express MPO; primary monocytes and the acute myelomonocytic leukemia cell line THP-1. Furthermore, these CTL lines also responded to MPO/HLA-A2-transfected HeLa cells. In contrast, negligible recognition was observed for the panel of HLA-A2pos antigen negative target cell lines, whereas responses in all cases again became apparent when these target cells were loaded with the relevant MPO peptide (FIG. 3).

CTL lines reactive to two additional MPO-derived peptides were generated from the same donor and tested functionally against a smaller selection of target cells in separate experiments. These CTL lines responded strongly to HLA-A2pos target cells endogenously expressing MPO, either naturally (monocytes, THP-1) or following genetic introduction (SupT1, HeLa), and to HLA-A2posMPOneg target cells loaded with relevant peptide (SupT1, T2, HEK, CD4pos T cells) (FIG. 5B,C). Negligible responses were seen to the MPOneg target cells in the absence of added antigen. Furthermore, strong responses and a high degree of specificity was confirmed for additional cell lines generated against 5 of the same MPO-derived peptides from a second donor (FIG. 5D, E).

Figure 6:
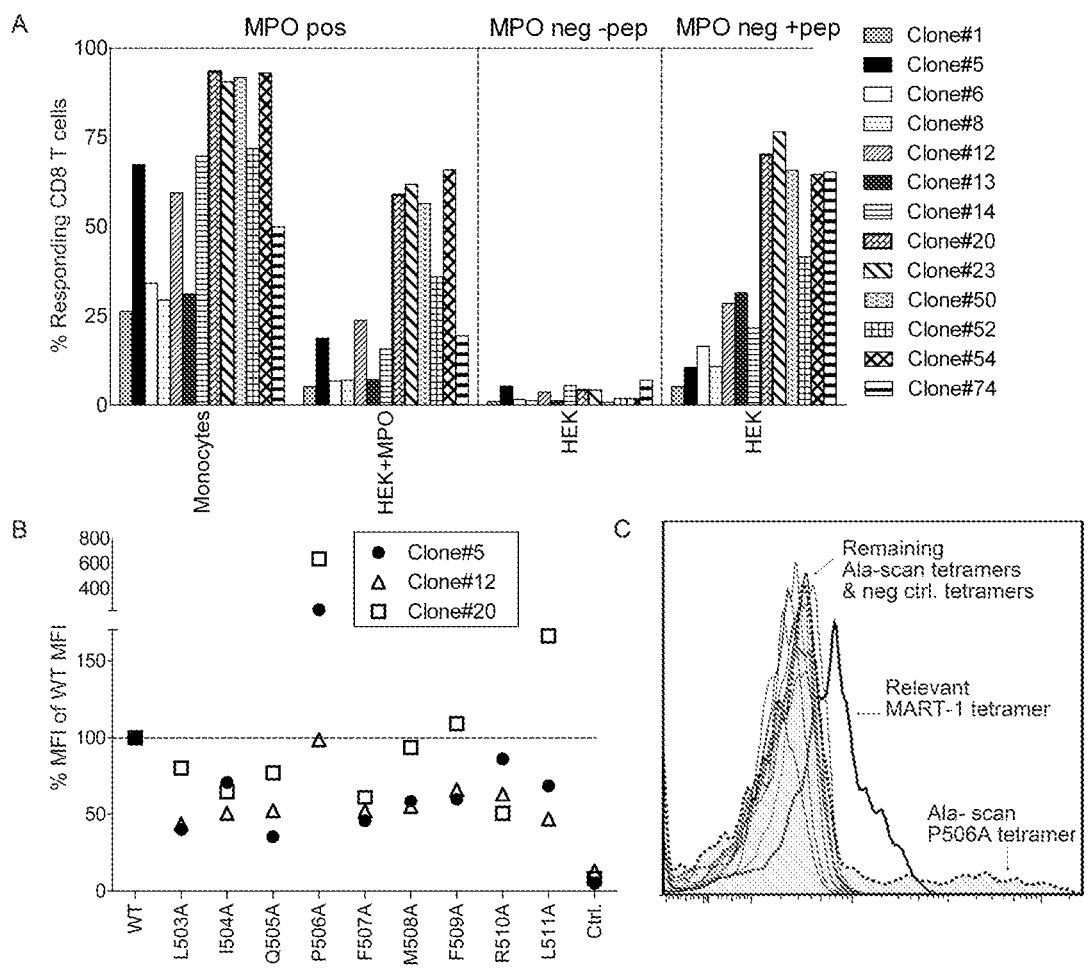
FIG. 6. T cell clones reactive to MPO peptide #25 show specific responses of variable magnitudes to HLA-A2posMPOpos target cells, and depend on multiple but different amino acids for peptide recognition. (A) Assays were performed as described in FIG. 2, except that only degranulation responses were measured. The bars show frequencies of CD107a/b positive cells of CD8posHLA-A2neg cells when indicated T cell clone was co-cultured with indicated target cells (x-axis). (B) Three of the clones shown in (A) were examined for binding of PE-conjugated HLA-A2 multimers containing the #25 peptide with and without an alanine substitution in each position, using flow cytometry. The negative control multimer (Ctrl) incorporated a CMV-derived peptide (NLVPMVATV (SEQ ID NO:75)). (C) Multimers incorporating alanine-replaced or WT peptides were tested for binding to primary T cells transduced with a MART-1 specific TCR, along with a multimer incorporating the cognate MART-1 peptide (ELAGIGILTV (SEQ ID NO:73)) as a positive control or the CMV-derived peptide as a negative control.

To obtain more information on the range of T cell reactivities to one of these novel T cell epitopes, T-cell clones were generated from CTL line #25, specific for MPO epitope LIQPFMFRL (SEQ ID NO:45). All CTL clones responded strongly to HLA-A2pos monocytes, whereas the responses to MPO-transfected or peptide-loaded HEK cells was variable, although in all cases higher than that observed for untransfected HEK cells (FIG. 6A). Sufficient cells were available for 3 of the clones to evaluate their fine specificity using HLA multimers containing peptides in which each of the amino acids in the MPO peptide #25 was individually replaced by an alanine residue. The results showed that the fine-specificity differed among the T cell clones, with the large majority of the substitutions leading to reduced multimer binding, although replacements in position 4 and 9 gave an increased binding (FIG. 6B). The higher binding seen with an alanine-replacement in position 4 (P506A) was, however, likely due to unspecific binding, as this particular multimer was the only one that bound non-specifically to primary T cells transduced with a MART-1 specific TCR (FIG. 6C).

Figure 9:
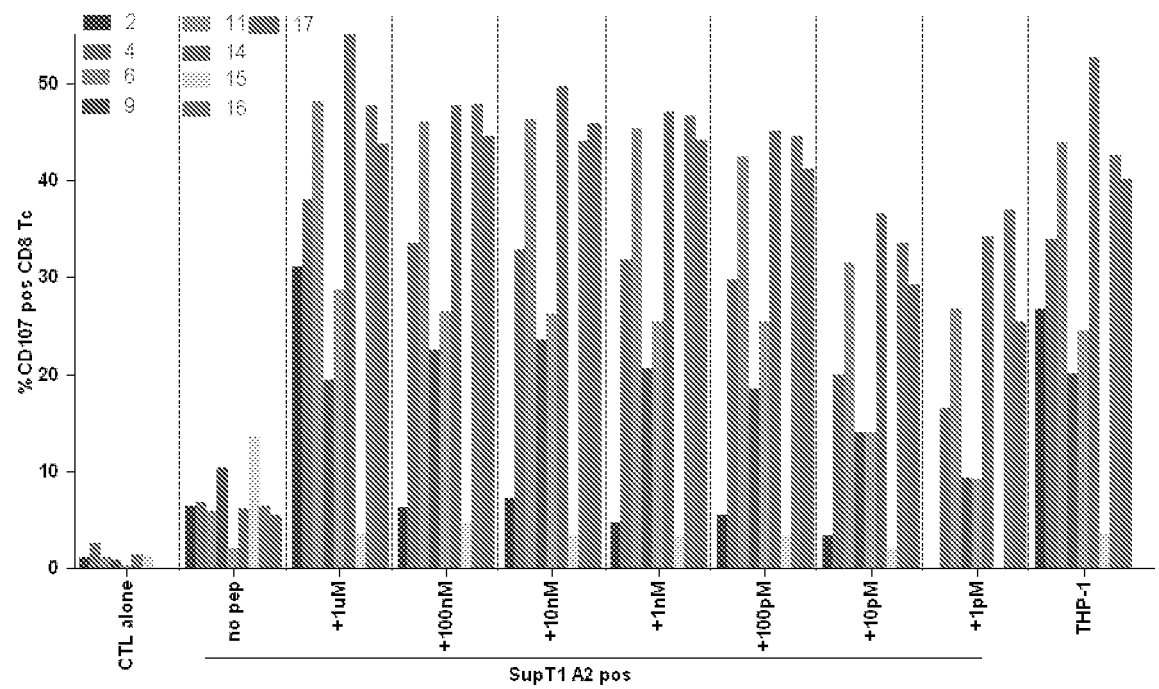
FIG. 9: MPO-reactive T cell clones recognize their specific target with high avidity. Clones (indicated by number) from cell line number 9 were co-cultured with the HLA-A2 positive MPO negative cell line SupT1 loaded with indicated concentrations of the cognate MPO peptide or not (no pep). The clones were also tested for recognition of endogenously presented peptide by co-culture with the HLA-A2 positive MPO positive myeloid leukemia cell line THP-1.

The high avidity of MPO-specific clones was additionally confirmed with clones from cell line #9 (FIG. 9). The clones responded to target cells loaded with peptide at concentrations down to 1 pM. Furthermore, they responded strongly to THP-1 cells endogenously presenting MPO (FIG. 9).

Figure 7:
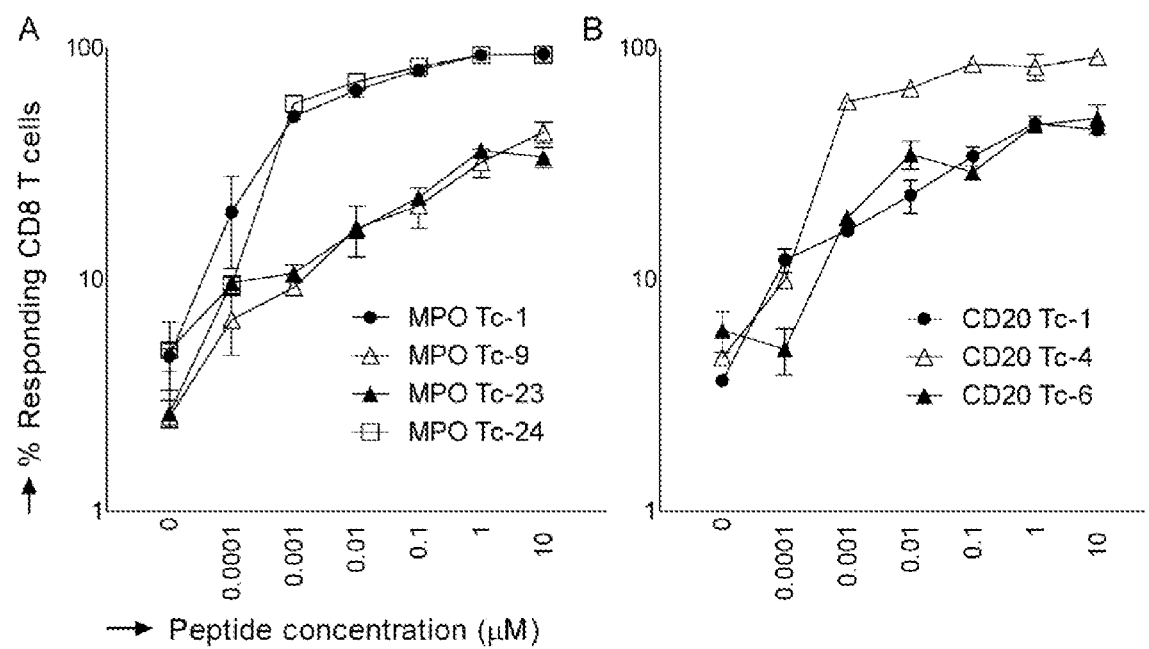
FIG. 7. CTL lines recognizing CD20 or MPO respond to low concentrations of peptide. CTL lines reactive to the MPO-derived peptides #1, 9, 23 or 24 (left graph), or to the CD20-derived peptides #1, 4 or 6 (right graph) were co-incubated with HLA-A2pos SupT1 cells loaded with indicated concentrations of cognate peptide. The assays were performed as described in FIG. 2. The symbols represent frequencies of CD107a/b and/or IFN-γ positive events among CD8pos HLA-A2neg T cells. Error bars represent SD of duplicates.

The strong HLA multimer binding and CTL responses that were induced to various target cells indicated high functional avidities. The CTL lines are, however, likely to consist of T cell clones displaying a wide variety of reactivities, as previously shown for allo-restricted T cell clones (9) and here for clones recognizing peptide #25. Nevertheless, when performing peptide titrations, reactivity was demonstrated at the lowest concentration (100 pM) for all but one of the tested CTL lines, indicating that for all, or nearly all, epitopes highly sensitive T cell populations can be obtained (FIG. 7).

In conclusion, we here demonstrate that a total of 18 CTL lines, reactive to 13 different peptides, strongly recognize their cognate antigens but do not show detectable cross reactivity against a large set of target cells that do not express this antigen. In addition, reactivity against 24 other CD20- and MPO-derived epitopes was observed, which was not pursued further here. Collectively, these results demonstrate that the majority of the algorithm-predicted peptides for CD20 and MPO were presented on the surface of cells endogenously expressing these proteins, thereby forming a broad repertoire of potential T cell targets. Moreover, the strong target reactivity and high degree of HLA- and peptide specificity indicates that such allo-reactive CTLs or their TCRs could be useful in a therapeutic setting.

TABLE 1

Peptides predicted to bind HLA-A*02:01 from CD20

| Peptide # | Position | Sequence | Predicted affinity (nM) |
|---|---|---|---|
| 1* | 187 | SLFLGILSV (SEQ ID NO: 1) | 9 |
| 2 | 115 | KMIMNSLSL (SEQ ID NO: 2) | 25 |
| 3 | 197 | LIFAFFQEL (SEQ ID NO: 3) | 26 |
| 4 | 55 | QIMNGLFHI (SEQ ID NO: 4) | 27 |
| 5 | 93 | YIISGSLLA (SEQ ID NO: 5) | 28 |
| 6 | 86 | PLWGGIMYI (SEQ ID NO: 6) | 29 |
| 7 | 122 | SLFAAISGM (SEQ ID NO: 7) | 33 |
| 8 | 69 | LMIPAGIYA (SEQ ID NO: 8) | 34 |
| 9 | 117 | IMNSLSLFA (SEQ ID NO: 9) | 36 |
| 10 | 189 | FLGILSVML (SEQ ID NO: 10) | 44 |
| 11 | 67 | GLLMIPAGI (SEQ ID NO: 11) | 55 |
| 12 | 153 | FIRAHTPYI (SEQ ID NO: 12) | 64 |
| 13 | 192 | ILSVMLIFA (SEQ ID NO: 13) | 67 |
| 14 | 130 | MILSIMDIL (SEQ ID NO: 14) | 114 |
| 15 | 91 | IMYIISGSL (SEQ ID NO: 15) | 116 |
| 16 | 134 | IMDILNIKI (SEQ ID NO: 16) | 154 |
| 17 | 56 | IMNGLFHIA (SEQ ID NO: 17) | 167 |
| 18 | 126 | AISGMILSI (SEQ ID NO: 18) | 170 |
| 19 | 129 | GMILSIMDI (SEQ ID NO: 19) | 306 |
| 20 | 184 | SIQSLFLGI (SEQ ID NO: 20) | 376 |

*Bae J., et al. Clin Cancer Res. 2004; 10: 7043-7052

TABLE 2

Peptides predicted to bind HLA-A*02:01 from myeloperoxidase

| Peptide # | Position | Sequence | Predicted affinity (nM) |
|---|---|---|---|
| 1 | 27 | KLLLALAGL (SEQ ID NO: 21) | 20 |
| 2 | 31 | ALAGLLAIL (SEQ ID NO: 22) | 31 |
| 3 | 117 | YLHVALDLL (SEQ ID NO: 23) | 29 |
| 4 | 131 | SLWRRPFNV (SEQ ID NO: 24) | 12 |
| 5 | 142 | VLTPAQLNV (SEQ ID NO: 25) | 41 |
| 6 | 570 | RLFEQVMRI (SEQ ID NO: 26) | 9 |
| 7 | 642 | WMGGVSEPL (SEQ ID NO: 27) | 24 |
| 8 | 28 | LLLALAGLL (SEQ ID NO: 28) | 144 |
| 9 | 30 | LALAGLLAI (SEQ ID NO: 29) | 433 |
| 10 | 52 | VLGEVDTSL (SEQ ID NO: 30) | 85 |
| 11 | 64 | SMEEAKQLV (SEQ ID NO: 31) | 484 |
| 12 | 97 | LLSYFKQPV (SEQ ID NO: 32) | 51 |
| 13 | 249 | LMFMQWGQL (SEQ ID NO: 33) | 315 |
| 14 | 257 | LLDHDLDFT (SEQ ID NO: 34) | 460 |
| 15 | 328 | QINALTSFV (SEQ ID NO: 35) | 324 |
| 16 | 340 | MVYGSEEPL (SEQ ID NO: 36) | 392 |
| 17 | 354 | NMSNQLGLL (SEQ ID NO: 37) | 399 |
| 18 | 368 | FQDNGRALL (SEQ ID NO: 38) | 277 |
| 19 | 380 | NLHDDPCLL (SEQ ID NO: 39) | 218 |
| 20 | 424 | RLATELKSL (SEQ ID NO: 40) | 227 |
| 21 | 447 | KIVGAMVQI (SEQ ID NO: 41) | 258 |
| 22 | 461 | YLPLVLGPT (SEQ ID NO: 42) | 401 |
| 23 | 484 | SVDPRIANV (SEQ ID NO: 43) | 156 |
| 24 | 488 | RIANVFTNA (SEQ ID NO: 44) | 469 |
| 25 | 503 | LIQPFMFRL (SEQ ID NO: 45) | 317 |

TABLE 2-continued

Peptides predicted to bind HLA-A*02:01 from myeloperoxidase

| Peptide # | Position | Sequence | Predicted affinity (nM) |
|---|---|---|---|
| 26 | 510 | RLDNRYQPM (SEQ ID NO: 46) | 482 |
| 27 | 528 | RVFFASWRV (SEQ ID NO: 47) | 51 |
| 28 | 537 | VLEGGIDPI (SEQ ID NO: 48) | 249 |
| 29 | 548 | GLMATPAKL (SEQ ID NO: 49) | 72 |
| 30 | 726 | FVNCSTLPA (SEQ ID NO: 50) | 55 |

Figure 4:
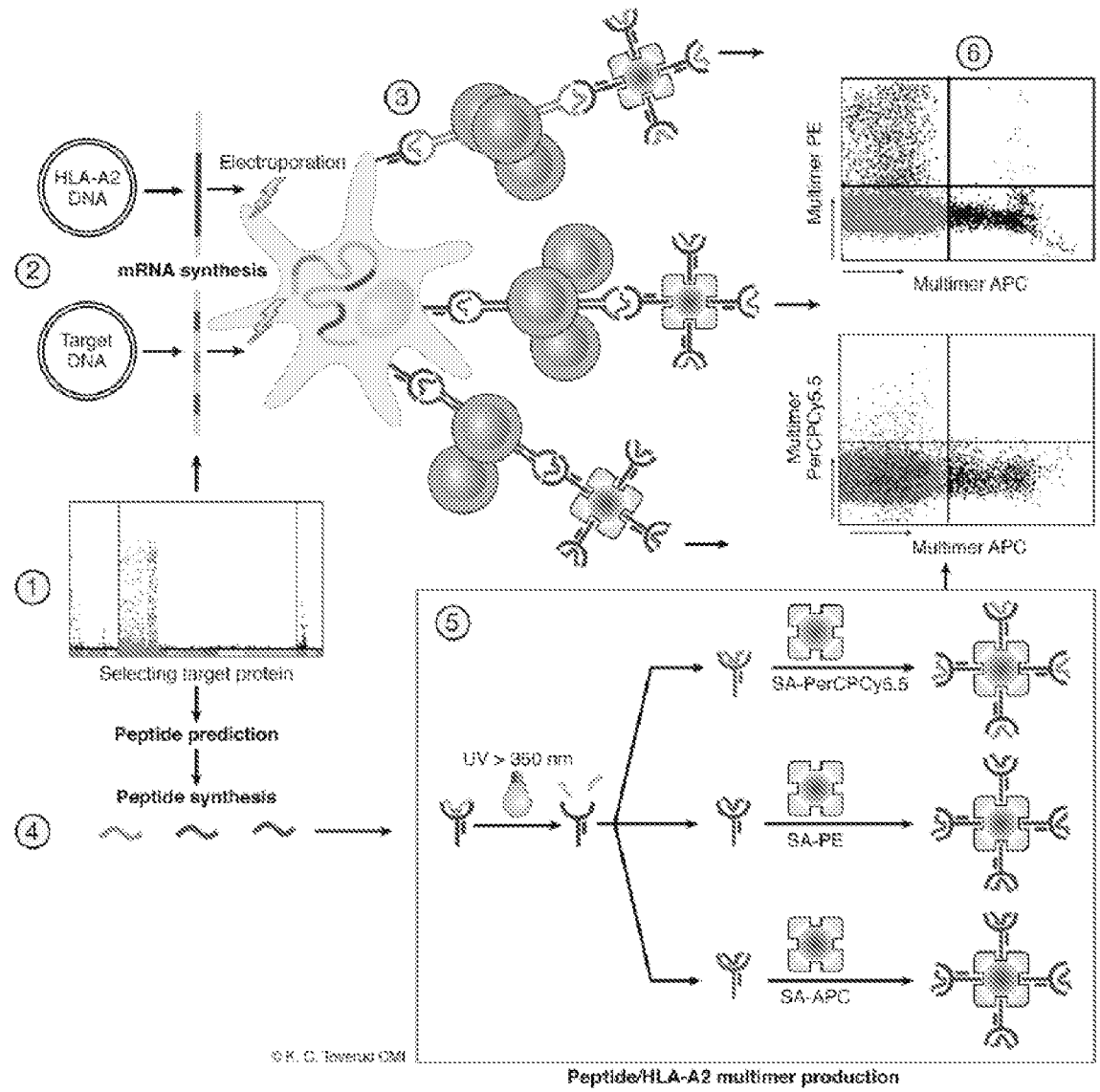
FIG. 4. Platform for high-throughput epitope discovery. (1) Candidate target proteins were screened for cell-type specific expression in normal and malignant hematopoietic cells (GeneSapiens.org). (2) Selected target proteins, and HLA-A*02:01, were cloned into a vector for in vitro production of mRNA encoding full-length protein. (3) Monocyte-derived dendritic cells from HLA-A2neg donors were transfected with the mRNA, and subsequently co-cultured with autologous, non-adherent peripheral blood mononuclear cells. The cultures were re-stimulated with EBV-LCLs transfected with mRNA encoding target protein and HLA-A2 on days 12 and 19. (4) Selected targets were subjected to affinity-based algorithmic prediction of HLA-A*02:01-restricted peptides (cbs.dtu.dk/services/NetMHC/) and those predicted to bind with the highest affinities were synthesized. (5) Peptides were complexed with HLA-A*02:01 monomers by UV-induced ligand exchange, followed by multimerization using streptavidin (SA) conjugated to PE, APC or PerCP-Cy5.5, respectively. (6) By end of culture, CD8pos T cells reactive to different epitopes were detected by flow cytometric measurements of combinations of fluorescently labeled pHLA-A2 multimers.

The results in the present study indicate that the self-immunopeptidome is more diverse than previously believed, and that a multitude of self-epitopes can be targeted by T cells. A surprisingly high fraction (74%) of peptides predicted to bind HLA from self-TAA were efficiently presented to CTLs, using the strategy presented here (FIG. 4). This resulted in the detection of 37 epitopes from one known (CD20) and one novel (MPO) cancer target, representing leukemia-associated differentiation antigens. Among these, 36 epitopes were novel. This output was striking, considering that only 250 HLA class I CTL cancer epitopes have been identified to date from non-melanoma-associated antigens (1). The epitopes identified in the present study were presented on leukemia cells and other target cells endogenously expressing the antigens, at levels sufficient to be efficiently recognized by T cells. These results indicate that algorithm-based predictions reflect the immunopeptidome more accurately than previously believed. Furthermore, it suggests that studies performed using mass spectrometry may underestimate MHC-associated peptide repertoires. Peptide ligands for HLA-A*02:01 have not been identified from the large majority of the on average 18,000 proteins expressed in a cell (10). In concert with this, none of the novel epitopes from CD20 and MPO were found in existing peptide databases, such as Syfpeithi (syfpeithi.de) and the Immune epitope database (iedb.org).

Our results have important implications for T-cell epitope discovery. Traditional cell-based methods typically involve cloning of patient T cells, followed by laborious screening of clones for reactivity against peptide libraries or fractions of peptide pools eluted from MHC molecules of target cells, and finally peptide characterization by MS (11, 12). Recently, color-coded pMHC-multimers (13) were used to screen tumor-infiltrating lymphocytes for reactivity against hundreds of known melanoma epitopes, thereby increasing throughput (1). However, all studies depending on patient cells for epitope discovery are limited by tolerance to self and previous immunization history of the individual. In contrast, the strategy presented here took advantage of induction of responses in T-cell repertoires from antigen-inexperienced, non-tolerized individuals. This suggests that the use of self-tolerant T-cell repertoires, rather than poor peptide presentation, is the reason why few cancer epitopes have been identified. In the current approach, induction of T-cell responses by DCs transfected with mRNA encoding full-length target proteins focused discovery on naturally presented peptides (14). Finally, detection of antigen-specific T cells by color-coded pHLA multimers complexed with in-silico predicted peptides secured high throughput.

The discovery of epitopes in self-TAA was based on alloreactive T cells. The concept that cancer cells can be targeted by T cells recognizing self-peptides presented by foreign HLA, was first described by Stauss and colleagues (15-17). Although these and other studies have shown that certain peptides can be specifically recognized when presented on allogeneic HLA (8, 9, 12, 18-23), it seemed possible that they represented exceptions, since there is also evidence that allo-restricted cells are more promiscuous with regard to peptide recognition (9, 18, 24-28). However, when assessing reactivity to a large number of epitopes at the single cell level, we did not find evidence indicating that peptide recognition on foreign HLA generally has a low specificity. First, T cells stimulated by CD20 or MPO did not react with large panels of irrelevant pHLA multimers. More importantly, functional responses were absent or very low when stimulating the CTL lines with a large panel of HLA-A2pos CD20neg/MPOneg target cells, representing different histologies and presenting thousands of peptides from endogenously expressed antigens (29) in addition to a wide range of allogeneic HLA molecules. In contrast, these target cells elicited efficient CTL degranulation when induced to express the relevant antigens or loaded with peptide. Finally, the CTLs responded strongly when incubated with leukemia cells and other target cells naturally expressing CD20 or MPO. Importantly, the results did not only reflect the characteristics of a few selected clones, but were representative of CTL lines reactive with 13 different peptide targets derived from two proteins. Collectively, the results from this study therefore support the view that specific peptide recognition on foreign HLA is the rule rather than the exception.

The adoptive transfer of donor-derived T cells to a patient in allogeneic hematopoietic stem cell transplantation can induce remission of leukemia by so-called graft-versus-leukemia effects (30). A requirement to avoid potentially detrimental graft-versus-host disease, is that the donor and recipient are HLA-matched. However, recent studies show that clinically beneficial T cells can be generated from a single donor for adoptive transfer to multiple patients that are only partially HLA-matched (31). Surprisingly, third-party EBV-specific T cells can eliminate EBV-associated post-transplantation lymphoma in spite of likely immune recognition and rejection of foreign HLA by the patient immune system (31). Interestingly, there is no evidence that such mismatched CTLs reactive to EBV (32-35) or cytomegalovirus (36) cause graft-versus-host disease. These results, and the results presented here, bear promise that antigen-specific allogeneic T cells reactive to self-TAA can be generated from a single HLA-A2neg donor for transfer to multiple HLA-A2pos patients. Alternatively, their receptors may be genetically transferred to redirect patient T cells to the tumor (37-39).

Elimination of normal and malignant B cells by anti-CD20 antibody treatment is well tolerated by patients. This indicates that the cytotoxic effects of CD20 specific T cells, although mechanistically different from that of antibodies, would also be tolerated. In contrast, the removal of myeloid cells in leukemia by MPOpos/HLA-A2pos specific T cells would result in significant toxicity unless accompanied by an allogeneic hematopoietic stem cell transplant from an HLA-A2neg donor. Such transplants, mismatched for one major HLA antigen, are accepted for high-risk patients in the clinic today, and would allow re-treatment of a potential relapse with MPO specific T cells while sparing the transplanted cells. The outlined platform for high-throughput epitope discovery provides an important solution to the first bottleneck in the clinical translation of the described concept, and warrants further testing of safety and efficacy in vivo.

By use of a novel technology platform we have identified a 36 novel cytotoxic T cell epitopes from two self-tumor associated antigens (self-TAA). For a high number of these—and for all epitopes tested—we have also demonstrated their potential utility as targets of cancer immunotherapy directly.

Example 2

Figure 8:
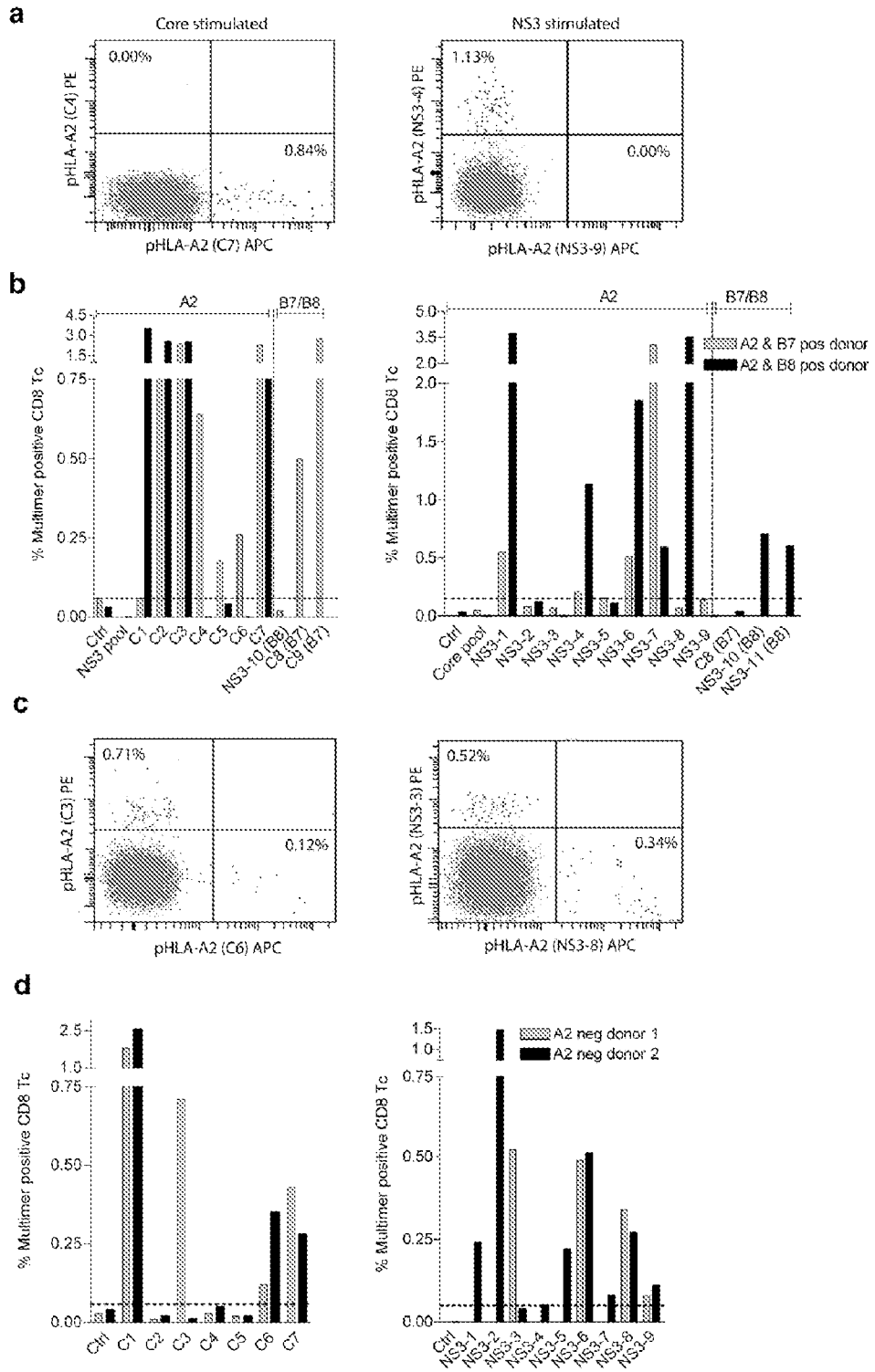
FIG. 8. Recognition of HCV antigens is similar when peptides are presented on autologous or foreign HLA. (A, B) Monocyte-derived DCs (moDCs) from HLA-A2$^{pos}$ donors were transfected with mRNA encoding HCV core (left) or NS3 antigens (right). The cells were co-cultured with autologous non-adherent PBMCs. On days 12 and 19, T cells were restimulated with autologous EBV-LCL transfected with the same HCV antigens. On day 26 co-cultures were stained with CD8 and pHLA-A2 multimers with indicated peptides from HCV core (C1-9) and HCV NS3 (N53-1-11), respectively, conjugated to PE or APC. Flow cytometric analysis of percentages of viable CD8$^{pos}$ T cells staining positively for indicated multimers is shown in (A) (black dots), or as bars in (B). Grey and black bars indicate cells obtained from HLA-A2$^{pos}$ donors co-expressing HLA-B7 or HLA-B8, respectively. Control multimers (ctrl; CMV and MART-1), NS3 pool (mix of multimers containing NS3-1, -2 or -6 peptides) and core pool (C1-3) were included to test specificity of staining, as was staining of cells from the HLA-B7$^{pos}$ donor with the NS3-10/HLA-B8 multimer, and staining of cells from the HLA-B8$^{pos}$ donor with the C8/HLA-B7 multimer, respectively. (C,D) MoDCs from two HLA-A2$^{neg}$ donors (grey and black bars, respectively) were co-transfected with HLA-A2 and core (left) or NS3 antigens (right). Autologous T cells were stimulated, and restimulated with transfected EBV-LCL and stained as described above. Percentages of viable CD8$^{pos}$ T cells staining positively for indicated multimers are shown in (C) (black dots), or as bars in (D). Horizontal dashed lines indicate cut-off.

The method described in Example 1 above and illustrated in FIG. 4 was used to test various peptide epitopes from Hepatitis C Virus (HCV) proteins. Monocyte-derived DCs (moDCs) from HLA-A2$^{pos}$ donors were transfected with mRNA encoding full-length HCV non-structural (NS) protein 3 or core Ag. The donors were HCV seronegative to ensure T cell repertoires that were unbiased by previous infection. The moDCs were co-cultured with autologous CD8$^{pos}$ T cells. To assess the epitope-coverage of the reactive T cells, we prepared a panel of color-coded peptide-HLA-A2 (pHLA) multimers containing 20 different peptides. Fifteen corresponded to previously characterized epitopes, whereas five were potentially novel epitopes predicted to be strong binders to HLA-A*02:01 by the computer algorithm NetMHC (IC50<50 nM) (Table 3). The T cells were probed with mixtures of pHLA multimers fluorescing in different colors (FIG. 8 A,B).

Collectively, the CTLs that were generated from two donors covered the majority of the tested specificities. This included all of the nine known epitopes in HCV core Ag, and seven out of six known and five novel epitopes in NS3 (FIG. 8 A,B). In addition to indicating a high degree of efficiency in presenting a multitude of epitopes, the pattern of multimer labelling suggested specificity for the cognate targets. First, the large majority of T cells bound a single type of multimer only (FIG. 8A). Second, T cells from HLA-B*08:01 or HLA-B*07:02 positive donors selectively bound multimers of the respective HLA molecules. Third, T cells stimulated by NS3 did not bind multimers containing peptides from core Ag, and vice versa (FIG. 8B).

Next, we examined the efficiency of the approach for detection of the HCV-derived epitopes when presented on foreign HLA. The described experiments were repeated using cells from HLA-A2$^{neg}$ donors. The moDCs were transfected with HLA-A2, which we have demonstrated is an efficient strategy for peptide presentation on allogeneic HLA (10), and co-transfected with HCV antigens prior to co-culture with autologous T cells. The results showed that HLA-A2$^{neg}$ T cells largely recognized the same epitopes as T cells from HLA-A2$^{pos}$ donors. Importantly, there was low cross-reactivity to irrelevant pHLA-A2 multimers (FIG. 8C,D). Furthermore, freshly isolated T cells from the same donors stained negatively with all multimers (data not shown). Thus, as revealed by pHLA multimer staining, peptides bound to a foreign HLA molecule appeared to be recognized with similar efficiencies and specificities as those bound to self-HLA class I molecules.

TABLE 3

Peptides predicted to bind HLA-A*02:01, -B*08:01 and -B*07:02 from HCV Core and NS3 antigens

| Peptide # | Position | Sequence | Predicted affinity (nM) | Reference |
|---|---|---|---|---|
| Core-Hepatitis C viral antigen | | | | |
| C1 | 177-185 | FLLALLSCL (SEQ ID NO: 51) | 9 | Jackson, M., et al. J Med. Virol. 1999; 58: 239-46 |
| C2 | 77-85 | AQPGYPWPL (SEQ ID NO: 52) | 25 | Anthony D. D., et al. Clin. Immunol. 2002; 103: 264-76 |
| C3 | 181-189 | LLSCLTVPA (SEQ ID NO: 53) | 35 | Urbani S., et al. Hepatology. 2002; 33: 1533-43 |
| C4 | 168-176 | NLPGCSFSI (SEQ ID NO: 54) | 36 | Löhr H. F., et al. J Hepatol. 1998; 29: 524-32 |
| C5 | 35-44 | YLLPRRGPRL (SEQ ID NO: 55) | 123 | Cerny A., et al. J Clin Invest. 1995; 95: 521-30 |
| C6 | 132-140 | DLMGYIPLV (SEQ ID NO: 56) | 14 | Cerny A., et al. J Clin Invest. 1995; 95: 521-30 |
| C7 | 178-187 | LLALLSCLTV (SEQ ID NO: 57) | 24 | Cerny A., et al. J Clin Invest. 1995; 95: 521-30 |
| C8 | 41-49 | GPRLGVRAT(B7) (SEQ ID NO: 58) | 34 | Koziel M. J., et al. J Virol. 1993; 67: 7522-32 |
| C9 | 111-119 | DPRRRSRNL(B7) (SEQ ID NO: 59) | 19 | Healey C., et al. Gastroenterology. 2002; 110: 1209 |
| NS3-Hepatitis C viral antigen | | | | |
| NS3-1 | 44-52 | FLATCINGV (SEQ ID NO: 60) | 6 | Wertheimer A. M., et al. Hepatology. 2003; 37: 577-89 |
| NS3-2 | 560-568 | YLVAYQATV (SEQ ID NO: 61) | 7 | Wentworth P. A., et al. Int Immunology. 1996; 8: 651-659 |
| NS3-3 | 517-525 | YMNTPGLPV (SEQ ID NO: 62) | 17 | |
| NS3-4 | 581-589 | QMWKCLIRL (SEQ ID NO: 63) | 17 | |
| NS3-5 | 425-433 | SVIDCNTCV (SEQ ID NO: 64) | 25 | |

TABLE 3-continued

Peptides predicted to bind HLA-A*02:01, -B*08:01 and -B*07:02 from HCV Core and NS3 antigens

| Peptide # | Position | Sequence | Predicted affinity (nM) | Reference |
|---|---|---|---|---|
| NS3-6 | 14-22 | LLGCIITSL (SEQ ID NO: 65) | 32 | |
| NS3-7 | 439-447 | FSLDPTFTI (SEQ ID NO: 66) | 42 | |
| NS3-8 | 48-56 | CINGVCWTV (SEQ ID NO: 67) | 66 | Cerny A. et al. J Clin Invest. 1995; 95: 521-30 |
| NS3-9 | 262-271 | TGSPITYSTY (SEQ ID NO: 68) | 34458 | Rosen H. R. et al. Transplantation. 2002; 74: 209-16 |
| NS3-10 | 370-378 | HSKKKCDEL (B8) (SEQ ID NO: 69) | 2240 | Koziel M. J. et al. J Clin Invest. 1995; 96: 2311-21 |
| NS3-11 | 586-594 | LIRLKPTLH (B8) (SEQ ID NO: 70) | 15525 | Wong D. K. et al. J Virol. 2001; 75: 1229-35 |

REFERENCES

1. Andersen R S, et al. (2012) Dissection of T-cell antigen specificity in human melanoma. Cancer Res 72(7):1642-1650.
2. Admon A & Bassani-Sternberg M (2011) The Human Immunopeptidome Project, a suggestion for yet another postgenome next big thing. Mol Cell Proteomics 10(10): O111 011833.
3. Rammensee H G, Falk K, & Rotzschke O (1993) Peptides naturally presented by MHC class I molecules. Annual review of immunology 11:213-244.
4. Stevanovic S & Schild H (1999) Quantitative aspects of T cell activation—peptide generation and editing by MHC class I molecules. Seminars in immunology 11(6): 375-384.
5. Hassan C, et al. (2013) The human leukocyte antigen-presented ligandome of B lymphocytes. Mol Cell Proteomics.
6. Nielsen M, et al. (2007) NetMHCpan, a method for quantitative predictions of peptide binding to any HLA-A and -B locus protein of known sequence. PloS one 2(8): e796.
7. de Verteuil D, Granados D P, Thibault P, & Perreault C (2012) Origin and plasticity of MHC I-associated self peptides. Autoimmunity reviews 11(9):627-635.
8. Stronen E, et al. (2009) Dendritic cells engineered to express defined allo-HLA peptide complexes induce antigen-specific cytotoxic T cells efficiently killing tumor cells. Scand J Immunol 69(4):319-328.
9. Wilde S, et al. (2009) Dendritic cells pulsed with RNA encoding allogeneic MHC and antigen induce T cells with superior antitumor activity and higher TCR functional avidity. Blood 114(10):2131-2139.
10. Shiina T, Hosomichi K, Inoko H, & Kulski J K (2009) The HLA genomic loci map: expression, interaction, diversity and disease. Journal of human genetics 54(1): 15-39.
11. Kessler J H & Melief C J (2007) Identification of T-cell epitopes for cancer immunotherapy. Leukemia 21(9): 1859-1874.
12. Amir A L, et al. (2011) Allo-HLA-reactive T cells inducing graft-versus-host disease are single peptide specific. Blood 118(26):6733-6742.
13. Hadrup S R, et al. (2009) Parallel detection of antigen-specific T-cell responses by multidimensional encoding of MHC multimers. Nat Methods 6(7):520-526.
14. Boczkowski D, Nair S K, Snyder D, & Gilboa E (1996) Dendritic cells pulsed with RNA are potent antigen-presenting cells in vitro and in vivo. J Exp Med 184(2): 465-472.
15. Sadovnikova E, Jopling L A, Soo K S, & Stauss H J (1998) Generation of human tumor-reactive cytotoxic T cells against peptides presented by non-self HLA class I molecules. Eur J Immunol 28(1):193-200.
16. Savage P, et al. (2004) Use of B cell-bound HLA-A2 class I monomers to generate high-avidity, allo-restricted CTLs against the leukemia-associated protein Wilms tumor antigen. Blood 103(12):4613-4615.
17. Gao L, Downs A M, & Stauss H J (2005) Immunotherapy with CTL restricted by nonself MHC. Methods in molecular medicine 109:215-228.
18. Felix N J, et al. (2007) Alloreactive T cells respond specifically to multiple distinct peptide-MHC complexes. Nat Immunol 8(4):388-397.
19. Housset D & Malissen B (2003) What do TCR-pMHC crystal structures teach us about MHC restriction and alloreactivity? Trends in immunology 24(8):429-437.
20. Udaka K, Tsomides T J, & Eisen H N (1992) A naturally occurring peptide recognized by alloreactive CD8+ cytotoxic T lymphocytes in association with a class I MHC protein. Cell 69(6):989-998.
21. Kronig H, et al. (2009) Allorestricted T lymphocytes with a high avidity T-cell receptor towards NY-ESO-1 have potent anti-tumor activity. Int J Cancer 125(3):649-655.
22. Abrahamsen I W, et al. (2012) T cells raised against allogeneic HLA-A2/CD20 kill primary follicular lymphoma and acute lymphoblastic leukemia cells. Int J Cancer 130(8):1821-1832.
23. Abrahamsen I W, et al. (2010) Targeting B cell leukemia with highly specific allogeneic T cells with a public recognition motif. Leukemia 24(11):1901-1909.
24. Guimezanes A, et al. (2001) Identification of endogenous peptides recognized by in vivo or in vitro generated alloreactive cytotoxic T lymphocytes: distinct characteristics correlated with CD8 dependence. Eur J Immunol 31(2):421-432.
25. Mazza C, et al. (2007) How much can a T-cell antigen receptor adapt to structurally distinct antigenic peptides? The EMBO journal 26(7):1972-1983.
26. Leisegang M, et al. (2010) MHC-restricted fratricide of human lymphocytes expressing survivin-specific transgenic T cell receptors. The Journal of clinical investigation 120(11):3869-3877.

27. Falkenburg W J, et al. (2011) Allogeneic HLA-A*02-restricted WT1-specific T cells from mismatched donors are highly reactive but show off-target promiscuity J Immunol 187(5):2824-2833.
28. Stanislawski T, et al. (2001) Circumventing tolerance to a human MDM2-derived tumor antigen by TCR gene transfer. Nat Immunol 2(10):962-970.
29. Engelhard V H, Brickner A G, & Zarling A L (2002) Insights into antigen processing gained by direct analysis of the naturally processed class I MHC associated peptide repertoire. Molecular immunology 39(3-4):127-137.
30. Kolb H J (2008) Graft-versus-leukemia effects of transplantation and donor lymphocytes. Blood 112(12):4371-4383.
31. Cooper L J (2010) Off-the-shelf T-cell therapy. Blood 116(23):4741-4743.
32. Barker J N, et al. (2010) Successful treatment of EBV-associated posttransplantation lymphoma after cord blood transplantation using third-party EBV-specific cytotoxic T lymphocytes. Blood 116(23):5045-5049.
33. Wynn R F, et al. (2005) Treatment of Epstein-Barr-virus-associated primary CNS B cell lymphoma with allogeneic T-cell immunotherapy and stem-cell transplantation. The lancet oncology 6(5):344-346.
34. Hague T, et al. (2002) Treatment of Epstein-Barr-virus-positive post-transplantation lymphoproliferative disease with partly HLA-matched allogeneic cytotoxic T cells. Lancet 360(9331):436-442.
35. Hague T, et al. (2007) Allogeneic cytotoxic T-cell therapy for EBV-positive posttransplantation lymphoproliferative disease: results of a phase 2 multicenter clinical trial. Blood 110(4):1123-1131.
36. Melenhorst J J, et al. (2010) Allogeneic virus-specific T cells with HLA alloreactivity do not produce GVHD in human subjects. Blood 116(22):4700-4702.
37. Schumacher T N (2002) T-cell-receptor gene therapy. Nat Rev Immunol 2(7):512-519.
38. Morgan R A, et al. (2006) Cancer regression in patients after transfer of genetically engineered lymphocytes. Science 314(5796):126-129.
39. Robbins P F, et al. (2011) Tumor regression in patients with metastatic synovial cell sarcoma and melanoma using genetically engineered lymphocytes reactive with NY-ESO-1. Journal of clinical oncology: official journal of the American Society of Clinical Oncology 29(7):917-924.
40. Lundegaard C, et al. (2008) NetMHC-3.0: accurate web accessible predictions of human, mouse and monkey MHC class I affinities for peptides of length 8-11. Nucleic acids research 36(Web Server issue):W509-512.
41. Toebes M, et al. (2006) Design and use of conditional MHC class I ligands. Nat Med 12(2):246-251.
42. Walchli S, et al. (2011) A practical approach to T-cell receptor cloning and expression. PloS one 6(11):e27930.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of screening for novel T cell epitopes and T cell receptors binding to said novel epitopes, comprising:
   a) expressing a polypeptide comprising one or more candidate self-antigens derived from a self-protein in an antigen presenting cell that expresses a defined HLA molecule by introducing a nucleic acid construct encoding said polypeptide into said antigen presenting cell;
   b) utilizing an affinity-based algorithmic prediction to identify a plurality of peptides from said polypeptide that are predicted to bind to said defined HLA molecule to provide predicted peptides;
   c) synthesizing said predicted peptides and contacting said defined HLA molecule with said synthesized predicted peptides to allow those peptides among said synthesized predicted peptides that exhibit binding to said defined HLA molecule to generate predicted peptide:defined HLA molecule complexes;
   d) forming a plurality of labelled complexes of said synthesized predicted peptide:defined HLA molecules from those predicted peptides that bind to said defined HLA molecules to provide a plurality of labelled predicted peptide:defined HLA molecule multimer complexes;
   e) obtaining donor T cells from a donor, wherein said defined HLA molecule is not expressed by said T cells;
   f) contacting said antigen-presenting cells with said donor T cells to provide induced T cells; and
   g) identifying one or more of said plurality of said labelled predicted peptide:defined HLA molecule multimer complexes binding to said donor T cells to identify multimer complexes containing novel epitopes that simultaneously bind said defined HLA molecule and T-cell receptors on said induced T cells based on detection of said label.

2. The method of claim 1, wherein said defined HLA molecule is naturally expressed in said antigen presenting cell.

3. The method of claim 1, wherein said defined HLA molecule is exogenously expressed in said antigen presenting cell.

4. The method of claim 1, wherein said defined HLA molecule is HLA-A*02:01.

5. The method of claim 1, wherein said nucleic acid construct is an mRNA construct.

6. The method of claim 1, wherein said nucleic acid construct is part of a viral vector.

7. The method of claim 1, wherein at least one of the one or more candidate self antigens is CD20 or myeloperoxidase.

8. The method of claim 1, wherein the one or more candidate self antigens is screened for cell-type specific expression in normal and disease-affected cells prior to said expressing.

9. The method of claim 1, wherein said forming comprises UV-induced ligand exchange and multimerization.

10. The method of claim 1, wherein said donor T cells binding said predicted peptide:defined HLA molecule complexes express a T-cell receptor that binds to said complex and wherein the method further comprises the step of cloning said T-cell receptor from one of said identified T-cells and modifying cells from a subject to express said T-cell receptor to provide modified cells.

11. The method of claim 1, wherein said nucleic acid construct is a DNA construct.

* * * * *